(12) United States Patent
Anthony et al.

(10) Patent No.: US 9,943,419 B2
(45) Date of Patent: Apr. 17, 2018

(54) SURGICAL METHOD FOR IMPLANTING A STEMLESS HUMERAL COMPONENT TO THE HUMERUS OF A PATIENT

(71) Applicant: DEPUY SYNTHES PRODUCTS, INC., Raynham, MA (US)

(72) Inventors: Sarah Anthony, Leesburg, IN (US); Scott Lubensky, Winona Lake, IN (US); Didier Poncet, Bron (FR); Chad Lawrence, Warsaw, IN (US); David M. Warlop, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 34 days.

(21) Appl. No.: 14/885,594

(22) Filed: Oct. 16, 2015

(65) Prior Publication Data
US 2016/0030197 A1    Feb. 4, 2016

Related U.S. Application Data

(63) Continuation of application No. 13/803,526, filed on Mar. 14, 2013, now Pat. No. 9,161,843, and a
(Continued)

(51) Int. Cl.
*A61F 2/40* (2006.01)
*A61F 2/46* (2006.01)
(Continued)

(52) U.S. Cl.
CPC ............ *A61F 2/4612* (2013.01); *A61B 17/15* (2013.01); *A61B 17/16* (2013.01);
(Continued)

(58) Field of Classification Search
CPC ...... A61F 2/30; A61F 2/40; A61F 5/00; A61F 2/38
USPC .......... 623/18.11, 19.11–20.13, 20.35–20.36, 623/22.11–22.2, 22.4–23.14; 606/86 R–89
See application file for complete search history.

(56) References Cited

U.S. PATENT DOCUMENTS

| 3,775,020 A | 11/1973 | Stoutenberg |
| 4,280,776 A | 7/1981 | Chaconas |

(Continued)

FOREIGN PATENT DOCUMENTS

| CN | 101959476 A | 1/2011 |
| EP | 2604227 A1 | 6/2013 |

(Continued)

OTHER PUBLICATIONS

International Search Report, International Application No. PCT/US2013/031164, dated Jul. 19, 2013, 4 pages.
(Continued)

*Primary Examiner* — Yashita Sharma
(74) *Attorney, Agent, or Firm* — Barnes & Thornburg LLP

(57) ABSTRACT

A stemless humeral component for replacing the humeral head of a patient's humerus includes a support flange having a number of cantilevered legs extending distally away from a bottom surface thereof. Instruments and methods for surgically installing the stemless humeral component are also disclosed.

16 Claims, 27 Drawing Sheets

Related U.S. Application Data continuation of application No. 13/803,514, filed on Mar. 14, 2013, now Pat. No. 9,320,619.

(60) Provisional application No. 61/618,385, filed on Mar. 30, 2012, provisional application No. 61/618,389, filed on Mar. 30, 2012.

(51) Int. Cl.

| | | |
|---|---|---|
| *A61B 90/50* | (2016.01) | |
| *A61B 17/17* | (2006.01) | |
| *A61B 17/15* | (2006.01) | |
| *A61B 17/16* | (2006.01) | |
| *A61B 17/3205* | (2006.01) | |
| *A61B 17/84* | (2006.01) | |
| *A61F 2/30* | (2006.01) | |
| *A61B 90/00* | (2016.01) | |

(52) U.S. Cl.
CPC ...... *A61B 17/1604* (2013.01); *A61B 17/1684* (2013.01); *A61B 17/1739* (2013.01); *A61B 17/1778* (2016.11); *A61B 17/32053* (2013.01); *A61B 90/06* (2016.02); *A61B 90/50* (2016.02); *A61F 2/4003* (2013.01); *A61F 2/4014* (2013.01); *A61F 2/4637* (2013.01); *A61F 2/4684* (2013.01); *A61B 17/842* (2013.01); *A61B 2090/034* (2016.02); *A61B 2090/3945* (2016.02); *A61F 2/40* (2013.01); *A61F 2002/30235* (2013.01); *A61F 2002/30332* (2013.01); *A61F 2002/30574* (2013.01); *A61F 2002/30579* (2013.01); *A61F 2002/30604* (2013.01); *A61F 2002/30616* (2013.01); *A61F 2002/30772* (2013.01); *A61F 2002/30904* (2013.01); *A61F 2002/4007* (2013.01); *A61F 2002/4018* (2013.01); *A61F 2002/4022* (2013.01); *A61F 2002/4029* (2013.01); *A61F 2002/4033* (2013.01); *A61F 2002/4037* (2013.01); *A61F 2002/4619* (2013.01); *A61F 2002/4624* (2013.01); *A61F 2002/4627* (2013.01); *A61F 2002/4628* (2013.01); *A61F 2002/4629* (2013.01); *A61F 2002/4658* (2013.01); *A61F 2002/4681* (2013.01)

(56) References Cited

U.S. PATENT DOCUMENTS

| | | | |
|---|---|---|---|
| 4,341,206 A | | 7/1982 | Perrett et al. |
| 4,410,089 A | | 10/1983 | Bortolani |
| 5,116,339 A | | 5/1992 | Glock et al. |
| 5,129,909 A | * | 7/1992 | Sutherland ........... A61B 17/155 606/53 |
| 5,250,051 A | | 10/1993 | Maryan |
| 5,356,414 A | | 10/1994 | Cohen et al. |
| 5,415,502 A | | 5/1995 | Dahlin |
| 5,431,657 A | | 7/1995 | Rohr |
| 5,609,642 A | | 3/1997 | Johnson et al. |
| 5,976,148 A | | 11/1999 | Charpenet et al. |
| 6,063,124 A | | 5/2000 | Amstutz et al. |
| 6,514,287 B2 | | 2/2003 | Ondrla et al. |
| 6,673,115 B2 | | 1/2004 | Resch et al. |
| 6,699,289 B2 | | 3/2004 | Iannotti et al. |
| 6,783,549 B1 | | 8/2004 | Stone et al. |
| 6,913,463 B2 | | 7/2005 | Blacklock |
| 7,153,070 B1 | | 12/2006 | Schroeder |
| 7,182,786 B2 | | 2/2007 | Justin et al. |
| 7,473,268 B2 | | 1/2009 | Zucherman et al. |
| 7,524,334 B2 | | 4/2009 | Haidukewych |
| 7,608,109 B2 | | 10/2009 | Dalla Pria |
| 7,648,530 B2 | | 1/2010 | Habermeyer et al. |
| 7,846,164 B2 | | 12/2010 | Castillo et al. |
| 8,231,682 B2 | | 7/2012 | Lafosse et al. |
| 8,425,614 B2 | | 4/2013 | Winslow et al. |
| 8,845,750 B2 | | 9/2014 | Slavitt |
| 9,161,843 B2 | | 10/2015 | Anthony et al. |
| 9,320,619 B2 | | 4/2016 | Anthony et al. |
| 2002/0016634 A1 | | 2/2002 | Maroney et al. |
| 2002/0095214 A1 | | 7/2002 | Hyde, Jr. |
| 2003/0028249 A1 | | 2/2003 | Baccelli et al. |
| 2003/0060884 A1 | | 3/2003 | Fell et al. |
| 2003/0149482 A1 | | 8/2003 | Michelson |
| 2004/0002769 A1 | | 1/2004 | Ferree |
| 2004/0073226 A1 | | 4/2004 | Cotting et al. |
| 2004/0147933 A1 | | 7/2004 | McGovern |
| 2004/0225367 A1 | | 11/2004 | Glien et al. |
| 2005/0075640 A1 | | 4/2005 | Collazo et al. |
| 2006/0142872 A1 | | 6/2006 | Klotz et al. |
| 2006/0149390 A1 | | 7/2006 | Long et al. |
| 2006/0189996 A1 | | 8/2006 | Orbay et al. |
| 2006/0241761 A1 | | 10/2006 | Gately |
| 2007/0005072 A1 | | 1/2007 | Castillo et al. |
| 2007/0078519 A1 | | 4/2007 | Klotz |
| 2007/0100458 A1 | | 5/2007 | Dalla Pria |
| 2007/0173946 A1 | | 7/2007 | Bonutti |
| 2007/0225367 A1 | | 9/2007 | Kammermeier et al. |
| 2008/0071302 A1 | | 3/2008 | Castillo et al. |
| 2008/0294268 A1 | | 11/2008 | Baum et al. |
| 2009/0228113 A1 | * | 9/2009 | Lang ............... A61F 2/30942 623/20.32 |
| 2009/0264889 A1 | | 10/2009 | Long et al. |
| 2010/0114326 A1 | | 5/2010 | Winslow et al. |
| 2011/0060342 A1 | | 3/2011 | Turner et al. |
| 2011/0130763 A1 | | 6/2011 | Aux Epaules et al. |
| 2012/0265315 A1 | | 10/2012 | Kusogullari et al. |
| 2012/0296439 A1 | | 11/2012 | Slavitt |
| 2013/0018475 A1 | | 1/2013 | Vanasse et al. |
| 2013/0018476 A1 | | 1/2013 | Katrana et al. |
| 2013/0261754 A1 | | 10/2013 | Anthony et al. |
| 2013/0282015 A1 | | 10/2013 | Lubensky et al. |
| 2013/0325136 A1 | | 12/2013 | Thomas et al. |
| 2014/0188231 A1 | | 7/2014 | Poncet et al. |
| 2016/0038295 A1 | | 2/2016 | Anthony et al. |
| 2016/0038296 A1 | | 2/2016 | Anthony et al. |
| 2016/0038297 A1 | | 2/2016 | Anthony et al. |
| 2016/0038310 A1 | | 2/2016 | Anthony et al. |
| 2016/0058561 A1 | | 3/2016 | Anthony et al. |
| 2016/0228264 A1 | | 8/2016 | Anthony et al. |

FOREIGN PATENT DOCUMENTS

| | | |
|---|---|---|
| FR | 2674122 A1 | 9/1992 |
| FR | 2970411 A1 | 7/2012 |
| GB | 2346573 A | 8/2000 |
| JP | 11128256 | 5/1999 |
| JP | 2003230584 | 8/2003 |
| JP | 2014515651 A | 7/2014 |
| WO | 0217822 A1 | 3/2002 |
| WO | 2007134690 A2 | 11/2007 |
| WO | 2012035266 A1 | 3/2012 |

OTHER PUBLICATIONS

Japanese Office Action issued in connection with Japanese Application No. 2015-503287, dated Sep. 30, 2016, 9 pages (with English language translation).

Japanese Search Report, Japanese Application No. 2017-084316, dated Jan. 9, 2018, 2 pages (with English language translation).

* cited by examiner

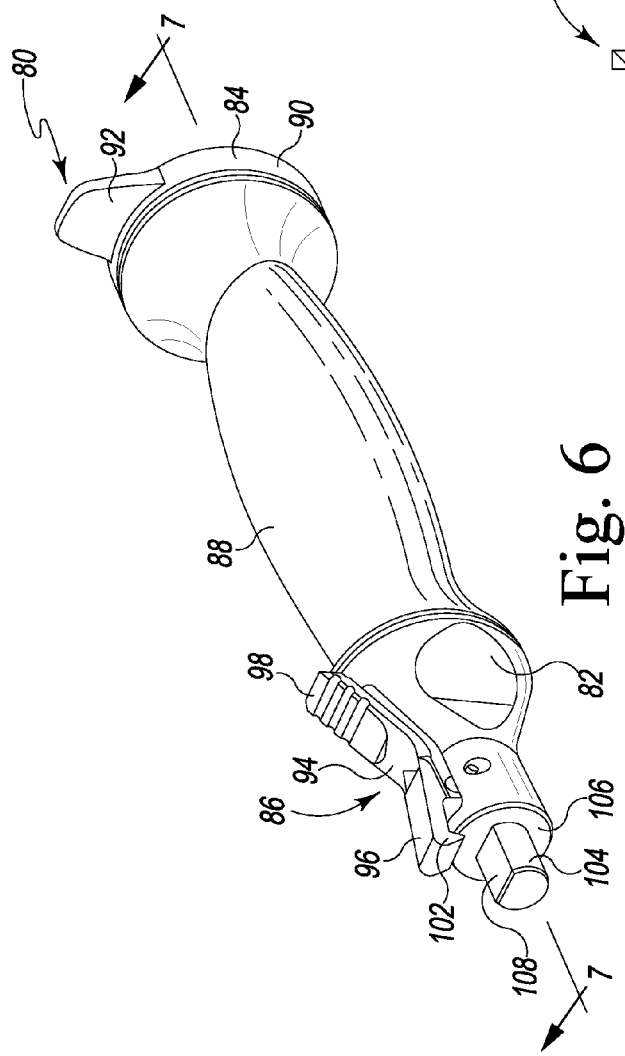
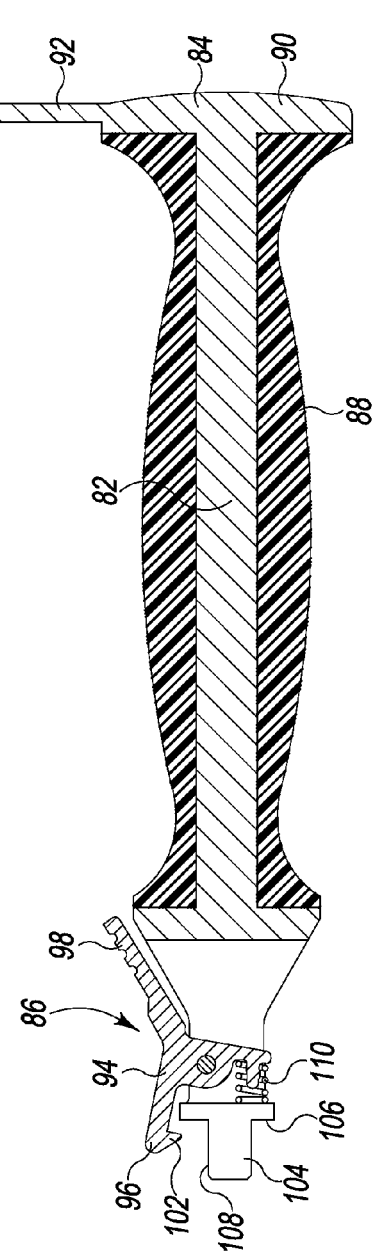
Fig. 6
Fig. 7

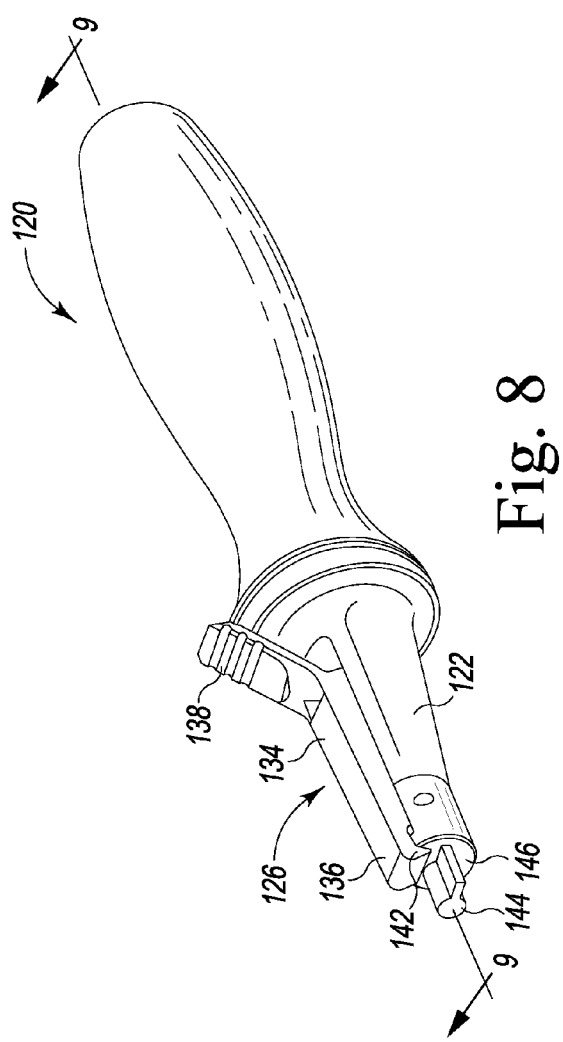
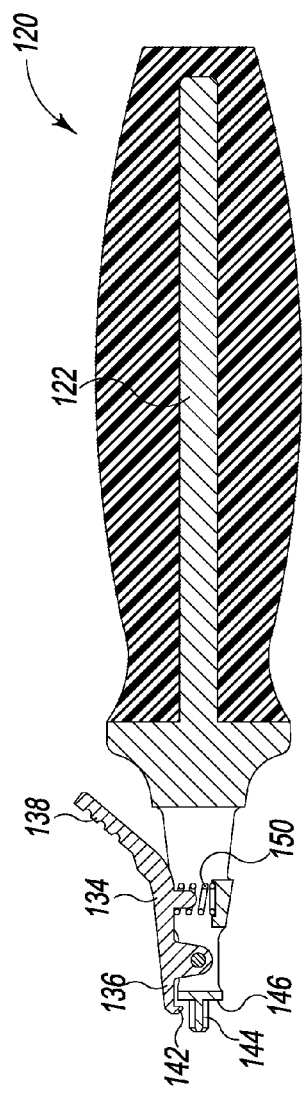
Fig. 8
Fig. 9

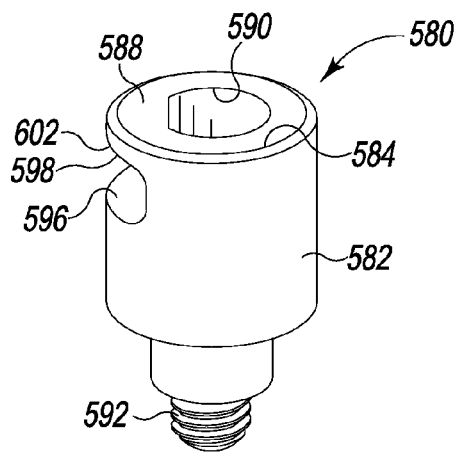
Fig. 38
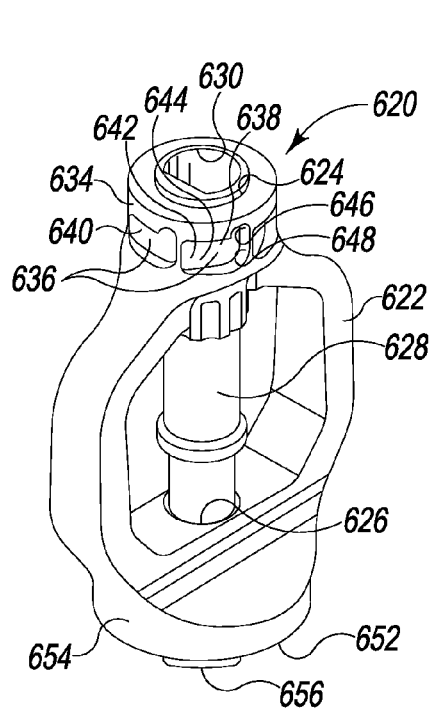 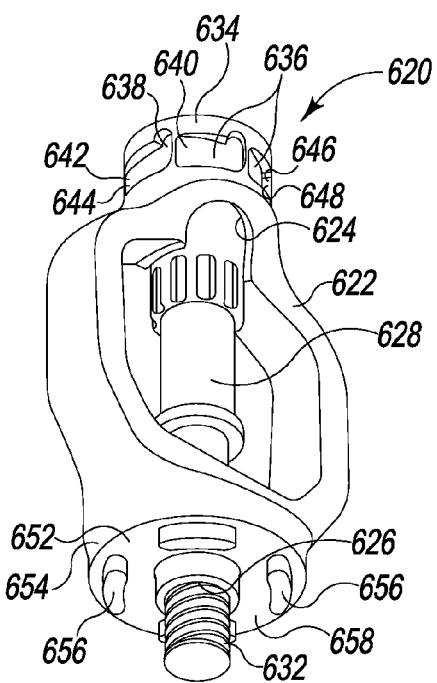
Fig. 39         Fig. 40

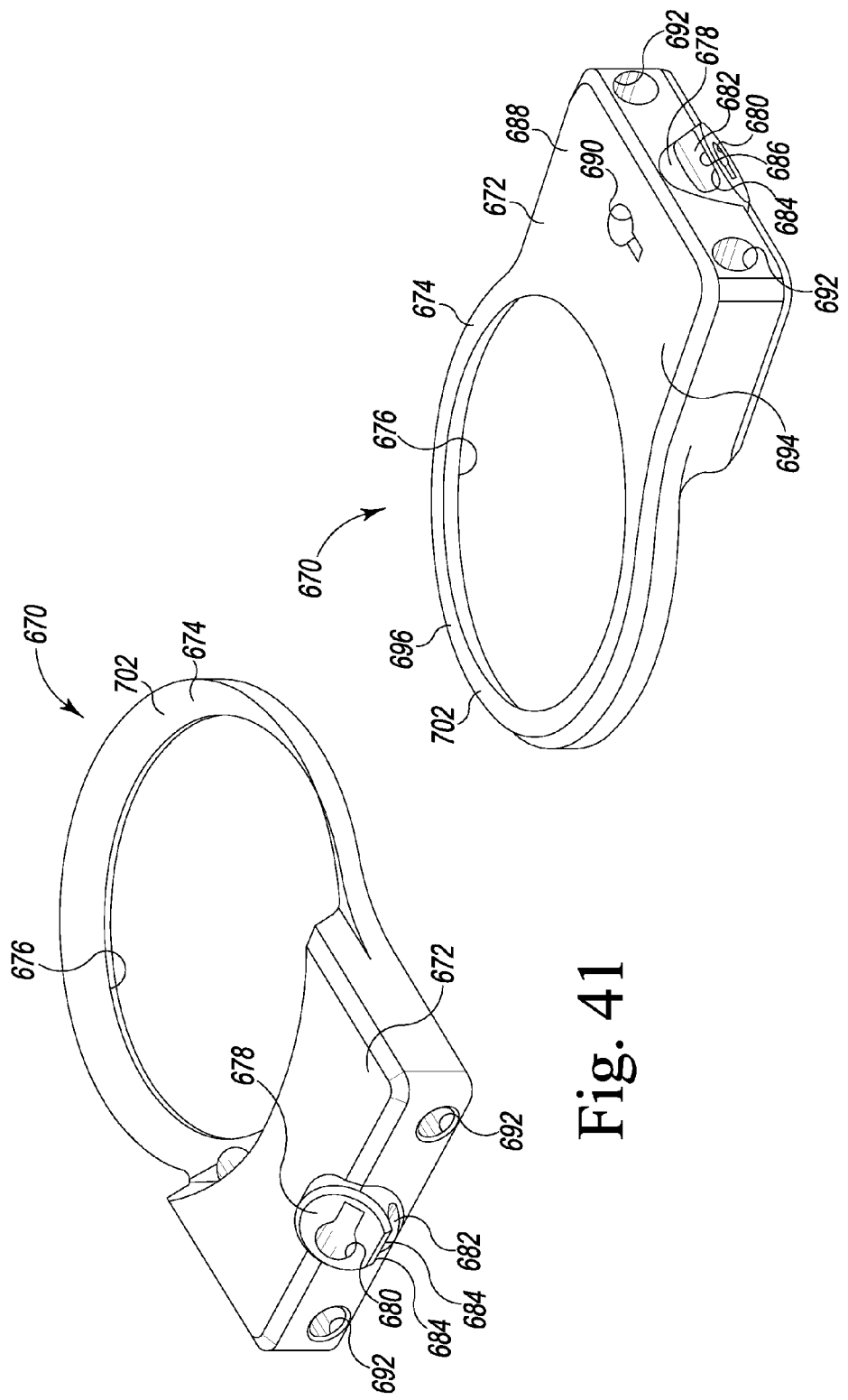

SURGICAL METHOD FOR IMPLANTING A STEMLESS HUMERAL COMPONENT TO THE HUMERUS OF A PATIENT

This application is a continuation of pending U.S. patent application Ser. No. 13/803,272, filed Mar. 14, 2013, which claims priority under 35 U.S.C. § 119 to U.S. Provisional Patent Application Ser. Nos. 61/618,385 and 61/618,389, both of which were filed on Mar. 30, 2012. Each of the above-identified applications is incorporated herein by reference.

CROSS REFERENCE

Cross reference is made to copending U.S. patent application Ser. No. 13/803,526 entitled "SURGICAL METHOD FOR IMPLANTING A STEMLESS HUMERAL COMPONENT TO THE HUMERUS OF A PATIENT"; copending U.S. patent application Ser. No. 13/803,514 entitled "SIZING INSTRUMENT AND PUNCH FOR USE IN A SURGICAL PROCEDURE TO IMPLANT A STEMLESS HUMERAL COMPONENT"; copending U.S. patent application Ser. No. 13/803,496 entitled "DRILL GUIDE FOR USE IN A SURGICAL PROCEDURE TO IMPLANT A STEMLESS HUMERAL COMPONENT"; and copending U.S. patent application Ser. No. 13/803,533 entitled "IMPLANT INSERTION TOOL FOR USE IN A SURGICAL PROCEDURE TO IMPLANT A STEMLESS HUMERAL COMPONENT", each of which is assigned to the same assignee as the present application, each of which was filed on Mar. 14, 2013, and each of which is hereby incorporated by reference.

Cross reference is also made to copending U.S. patent application Ser. No. 14/885,559 entitled "STEMLESS HUMERAL COMPONENT OF AN ORTHOPAEDIC SHOULDER PROSTHESIS"; copending U.S. patent application Ser. No. 14/885,635 entitled "SIZING INSTRUMENT FOR USE IN A SURGICAL PROCEDURE TO IMPLANT A STEMLESS HUMERAL COMPONENT"; copending U.S. patent application Ser. No. 14/885,435 entitled "STEMLESS HUMERAL COMPONENT OF AN ORTHOPAEDIC SHOULDER PROSTHESIS"; copending U.S. patent application Ser. No. 14/885,451 entitled "STEMLESS HUMERAL COMPONENT OF AN ORTHOPAEDIC SHOULDER PROSTHESIS"; and copending U.S. patent application Ser. No. 14/885,544 entitled "STEMLESS HUMERAL COMPONENT OF AN ORTHOPAEDIC SHOULDER PROSTHESIS", each of which is assigned to the same assignee as the present application, each of which is filed concurrently herewith, and each of which is hereby incorporated by reference.

TECHNICAL FIELD

The present disclosure relates generally to orthopaedic implants, instruments, and surgical methods, and more particularly to a stemless humeral component of an orthopaedic shoulder implant, along with its associated surgical instruments and methods.

BACKGROUND

During the lifetime of a patient, it may be necessary to perform a shoulder replacement procedure on the patient as a result of, for example, disease or trauma. In a shoulder replacement procedure, a humeral prosthesis is used to replace the natural head of the patient's humerus. The humeral prosthesis typically includes an elongated stem component that is implanted into the intramedullary canal of the patient's humerus and a generally hemispherically-shaped prosthetic head component that is secured to the stem component. In some shoulder replacement procedures, the natural glenoid surface of the scapula may be resurfaced or otherwise replaced with a glenoid component that provides a bearing surface upon which the prosthetic head component of the humeral prosthesis articulates.

SUMMARY

According to one aspect, a stemless humeral component is used as a substitute for a conventional humeral intramedullary stem component. In such a way, the stemless humeral component functions as a mounting structure for a humeral head component, but does so without removal of bone tissue from the intramedullary canal of the patient's humerus as would be the case with a conventional humeral stem component.

In an embodiment, the stemless humeral component includes a support flange having a number of cantilevered legs extending distally away from a bottom surface thereof. Each of the legs may be generally T-shaped when viewed from a bottom elevational view.

The stemless humeral component may have a number of viewing windows formed therein to allow the surgeon to visualize the surgically-prepared humeral surface (i.e., the surface created by surgically resecting the humeral head) to ensure the stemless humeral component is fully seated during surgical implantation thereof. The stemless humeral component may have a number of revision slots formed therein that permit a surgeon to pass an osteotome or other cutting instrument to cut or otherwise break the bony ongrowth, thereby facilitating removal of the stemless humeral component during a revision procedure.

The stemless humeral component may also include an elongated sleeve extending distally away from the bottom surface of its support flange. The sleeve may have a tapered bore formed therein. A tapered post of the humeral head component may be inserted into, and thereafter further urged into, the tapered bore of the stemless humeral component's elongated sleeve so as to taper lock the humeral head component to the stemless humeral component.

According to another aspect, an impaction handle may be used in a surgical procedure to implant the stemless humeral component. The impaction handle includes an attachment mechanism that allows the handle to be secured to a number of different instruments used during a surgical procedure to implant the stemless humeral component.

According to another aspect, an alignment handle may be used in a surgical procedure to implant the stemless humeral component. Like the impaction handle, the alignment handle includes an attachment mechanism that allows the handle to be secured to a number of different instruments used during a surgical procedure to implant the stemless humeral component.

According to another aspect, a sizing instrument may be used in a surgical procedure to implant the stemless humeral component. The sizing instrument is generally dome-shaped and may be secured to the patient's surgically-prepared humeral surface during a procedure to implant the stemless humeral component to function as both a sizing trial and a punch and drill guide.

According to another aspect, a trial head component is used for fit assessment during a surgical procedure to implant the stemless humeral component. It may also function as a trial instrument for the humeral head component, and, as such, includes a generally hemispherically-shaped body. The trial head component may also function as a drill guide for guiding a drill bit used to drill (or pre-drill) the holes in the patient's surgically-prepared humeral surface to receive the legs of the stemless humeral component.

According to yet another aspect, a surgical punch may be used to punch holes in the patient's surgically-prepared humeral surface to receive the legs of the stemless humeral component. In an embodiment, the surgical punch is generally fork-shaped and includes a number of tines that correspond in shape, size, and location with the legs of the stemless humeral component.

According to another aspect, a center drill bit may be used to surgically drill (or pre-drill) a hole in the patient's surgically-prepared humeral surface to receive the elongated sleeve of the stemless humeral component. A peripheral drill bit, on the other hand, may be used to drill (or pre-drill) the holes in the patient's surgically-prepared humeral surface to receive the legs of the stemless humeral component.

According to another aspect, an adjustable head resection guide may be used as a cutting guide to guide the advancement of a bone saw blade to resect the humeral head of the patient. The head resection guide may include an arcuate-shaped, stationary cutting guide secured and a movable cutting guide that is movable in a direction toward and away from the stationary cutting guide. In such a way, the adjustable head resection guide may function as a universally-sized instrument.

According to another aspect, a non-adjustable head resection guide may be used as a cutting guide to guide the advancement of a bone saw blade to resect the humeral head of the patient. The head resection guide may include a generally rectangular-shaped base having a circular-shaped ring secured thereto. The ring may extend outwardly from the base and define a circular-shaped opening. The patient's humeral head may be captured in the opening during resection thereof.

According to a further aspect, an implant insertion tool may be used to facilitate implantation of the stemless humeral component into the patient's surgically-prepared humeral surface. In an embodiment, the implant insertion tool functions as a "quick connect" instrument having a locked position in which the stemless humeral component is locked thereto, and an unlocked position in which the stemless humeral component is released therefrom. In another embodiment, the implant insertion tool may include a locking rod configured to be threadingly-engaged with the stemless humeral component. In another embodiment, the implant insertion tool may include a threaded end that is configured to engage the stemless humeral component and an aperture sized to receive a connecting pin of an impaction handle. In yet another embodiment, the implant insertion tool may include a locking rod configured to be threadingly-engaged with the stemless humeral component and an aperture sized to receive a connecting pin of an impaction handle.

According to another aspect, a head impaction tool may be used to impact, and hence taper lock, the head component to the stemless humeral component. The head impaction tool may include a rounded, concave impact surface that is sized, shaped, and positioned to closely conform to the convex, generally hemispherically-shaped outer surface of the head component.

BRIEF DESCRIPTION OF THE DRAWINGS

The detailed description particularly refers to the following figures, in which:

FIG. 6 is a perspective view of an impaction handle that may be used in a surgical procedure to implant the stemless humeral component of FIG. 1;

FIG. 7 is a cross-sectional view of the impaction handle taken along the line 7-7 of FIG. 6, as viewed in the direction of the arrows;

FIG. 8 is a perspective view of an alignment handle that may be used in a surgical procedure to implant the stemless humeral component of FIG. 1;

FIG. 9 is a cross-sectional view of the alignment handle taken along the line 9-9 of FIG. 8, as viewed in the direction of the arrows;

FIG. 38 is a perspective view of a different implant insertion tool that may be used in a surgical procedure to implant the stemless humeral component of FIG. 1;

FIGS. 39 and 40 are perspective views of yet another implant insertion tool that may be used in a surgical procedure to implant the stemless humeral component of FIG. 1;

FIGS. 41 and 42 are perspective views of another head resection guide that may be used in a surgical procedure to implant the stemless humeral component of FIG. 1;

DETAILED DESCRIPTION OF THE DRAWINGS

Figure 1:
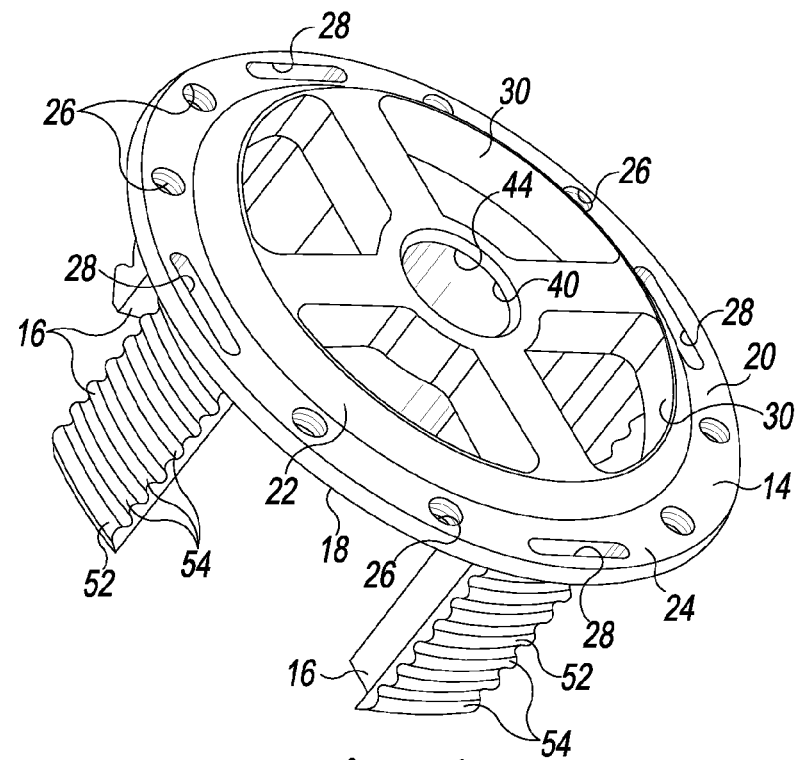
FIG. 1 is a medial perspective view of stemless humeral component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, et cetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-5, there is shown a stemless humeral component 10. As will be described in more detail below, the stemless humeral component 10 is used as a substitute for a conventional humeral intramedullary stem component. In such a way, the stemless humeral component 10 functions as a mounting structure for a humeral head component 12 (see FIGS. 35 and 36), but does so without removal of bone tissue from the intramedullary canal of the patient's humerus as would be the case with a conventional humeral stem component.

The stemless humeral component 10 includes a support flange 14 having a number of legs 16 extending distally away from a bottom surface 18 thereof. In the illustrative embodiment described herein, the support flange 14 is circular in shape. The top surface 20 of the support flange 14 includes an annular-shaped, beveled surface 22. An annular ring 24 extends around the periphery of the support flange's beveled surface 22. The annular ring 24 has a number of suture holes 26 formed therein. The suture holes 26 may be used to suture bone wafers or soft tissue to the stemless humeral component 10. For example, the natural attachment of the patient's rotator cuff may be preserved by harvesting a bone wafer around it and then suturing such a bone wafer to the stemless humeral component 10 by use of the suture holes 26.

Figure 4:
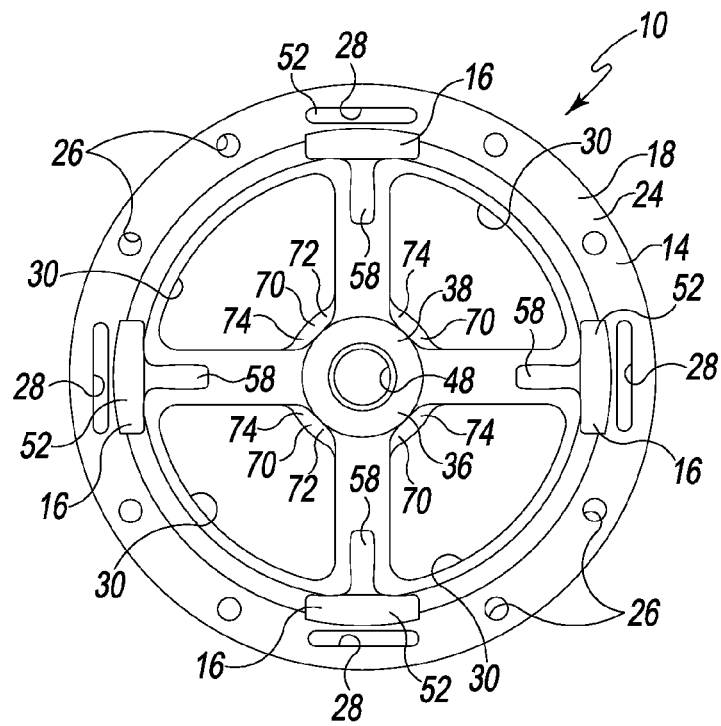
FIG. 4 is a lateral elevational view of the stemless humeral component of FIG. 1.

The support flange's annular ring 24 also has a number of revision slots 28 formed therein. As can be seen in FIGS. 1 and 4, one of the revision slots 28 is positioned on the annular ring 24 at a location above, and radially outwardly from, each of the legs 16. In such a way, an osteotome or other cutting instrument may be passed through the revision slots to cut or otherwise break the bony ongrowth to the legs 16 thereby facilitating removal of the stemless humeral component 10 during a revision procedure.

The support flange 14 also has a number of viewing windows 30 formed therein. The viewing windows 30 allow the surgeon to visualize the surgically-prepared humeral surface (i.e., the surface created by surgically resecting the humeral head) to ensure the stemless humeral component 10 is fully seated during surgical implantation thereof. It should be appreciated that the viewing windows 30 may also function as additional revision slots through which the surgeon may pass an osteotome or other cutting instrument slots to cut or otherwise break the bony ongrowth to the legs 16 thereby facilitating removal of the stemless humeral component 10 during a revision procedure.

Figure 2:
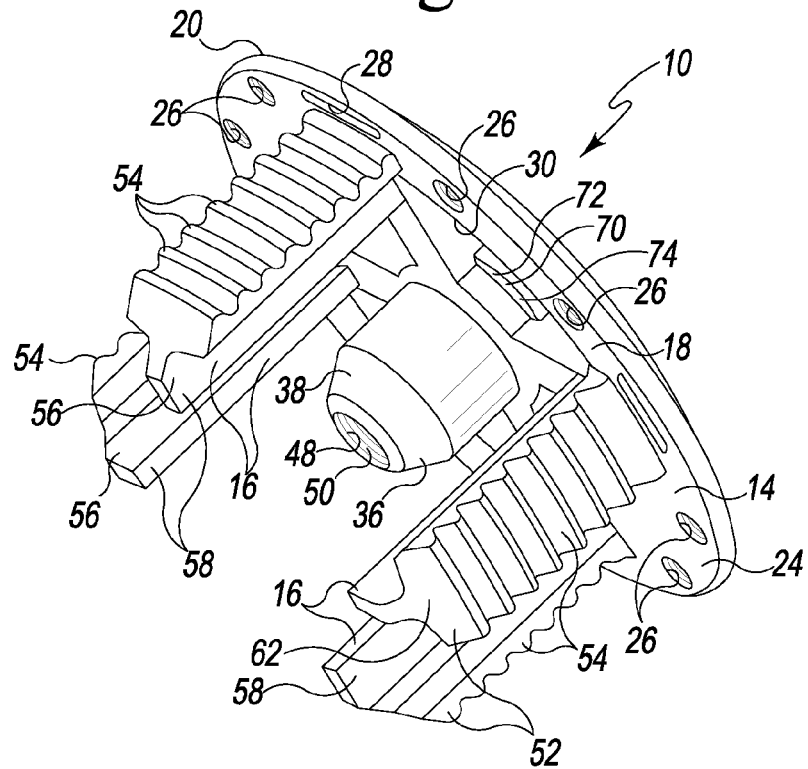
FIG. 2 is a lateral perspective view of the stemless humeral component of FIG. 1.
Figure 3:
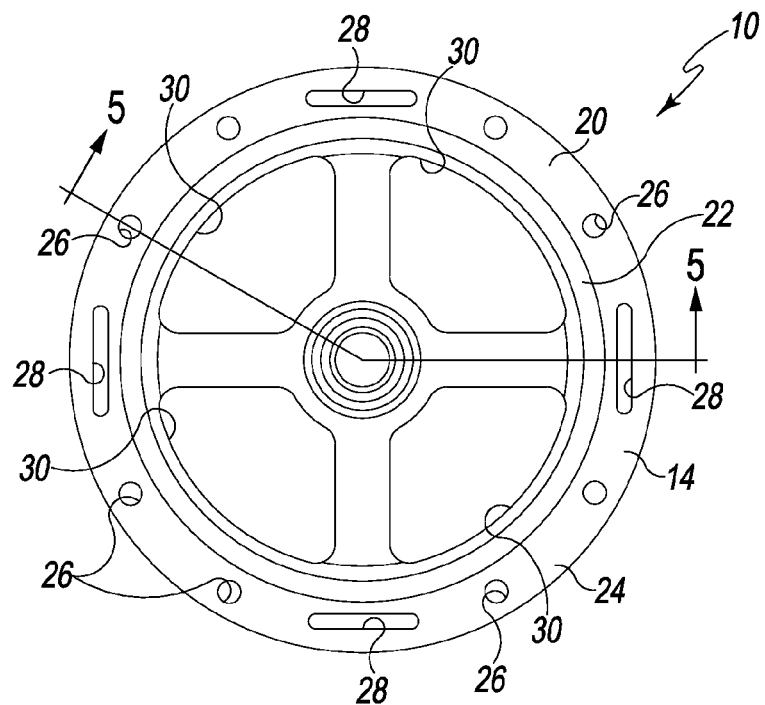
FIG. 3 is a medial elevational view of the stemless humeral component of FIG. 1.
Figure 5:
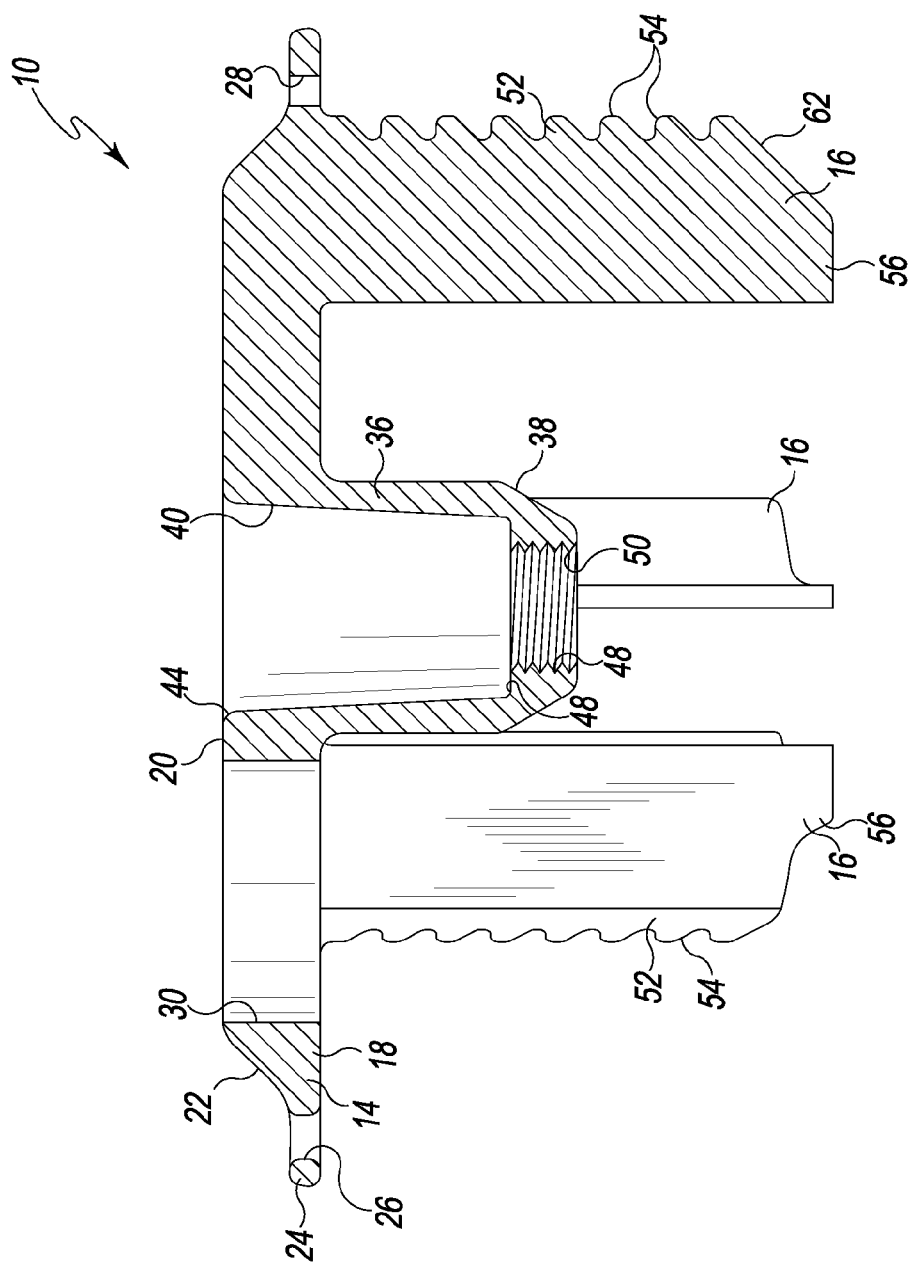
FIG. 5 is an enlarged cross-sectional view of the stemless humeral component taken along the line 5-5 of FIG. 3, as viewed in the direction of the arrows.

As can be seen in FIGS. 2 and 5, an elongated sleeve 36 extends distally away from a bottom surface 18 of the support flange 14 in the same general direction as the legs 16. The sleeve 36 includes a tapered distal end 38 that functions as a lead-in to facilitate insertion into a hole drilled or otherwise formed in the patient's surgically-prepared humeral surface (i.e., the surface created by surgically resecting the humeral head). The elongated sleeve 36 has a tapered bore 40 formed therein. A tapered post 42 extends laterally out of the backside surface of the humeral head component 12 (i.e., the side opposite the humeral head component's generally hemispherically-shaped outer bearing surface) and is received into the tapered bore 40 of the stemless humeral component's elongated sleeve 36 (see FIG. 36). As will be discussed below in greater detail below, urging the tapered post 42 of the humeral head component 12 into contact with the sidewall defining the tapered bore 40 of the elongated sleeve 36 taper locks the humeral head component 12 to the stemless humeral component 10. As can be seen in FIG. 5, the upper end 44 of the tapered bore 40 opens into the top surface 20 of the support flange 14, with the lower, distal end 46 of the tapered bore 40 opening into a threaded bore 48. The threaded bore 48 extends distally away from the distal end 46 of the tapered bore 40 and opens into the distal end 38 of the elongated sleeve 36. As can be seen in FIG. 5, a number of threads 50 are formed in the sidewall that defines the threaded bore 48. The threads 50 are sized to match, and hence threadingly receive, the threads of an implant retraction tool (not shown) or, as discussed in more detail below, an implant insertion tool.

As can be seen in FIGS. 2, 4, and 5, each of the legs 16 is cantilevered and, as a result, includes one end secured to the bottom surface 18 of the support flange 14 with the other end of the leg 16 being free (i.e., not secured to the support flange 14, any of the other legs 16, or any other structure of the stemless humeral component 10). As can also be seen in FIGS. 2, 4, and 5, each of the legs 16 is generally T-shaped when viewed from a bottom elevational view (i.e., a view that is orthogonal to the longitudinal axis of the leg 16) and, as a result, has a T-shaped lateral cross section (i.e., a cross section taken in the plane orthogonal to the longitudinal axis of the leg). In such an arrangement, each of the legs 16 has a bone-engaging plate 52 having a number of serrations 54 formed in a side thereof that faces outwardly from the elongated sleeve 36 (and hence the center of the support flange 14). As can be seen best in FIG. 5, each of the serrations 54 is angled upwardly in a direction toward the support flange 14 (i.e., in a direction away from the distal end 56 of the leg 16). When implanted in bone tissue, such upwardly angled serrations 54 engage the bone tissue in a manner that resists pullout of the stemless humeral component 10. An elongated rib 58 extends along the length of the engaging plate 52 and, as such, forms the "trunk" of the T-shaped leg 16, with the bone-engaging plate 52 forming its "cross bar". Specifically, the rib 58 is secured to the backside of the leg's engaging plate 52 (i.e., the side opposite the serrations 54) and extends inwardly in the direction toward the center of the support flange 14. The longitudinal axis of the rib 58 is parallel with the longitudinal axis of the engaging plate 52. As can be seen in FIGS. 2 and 5, each of the legs 16 includes a beveled distal end 62 that functions as a lead-in to facilitate insertion of the leg 16 into a hole punched or otherwise formed in the patient's surgically-prepared humeral surface (i.e., the surface created by surgically resecting the humeral head).

As can be seen best in FIGS. 2 and 4, the bottom surface 18 of the stemless humeral component's support flange 14 has a number of undercuts 70 formed therein. In the illustrative embodiment described herein, the undercuts 70 are positioned radially around the elongated sleeve 36 about 90° from one another. As can be seen in FIGS. 2 and 4, the position of the undercuts 70 coincides with the radial position of each of the viewing windows 30. Specifically, the undercuts 70 are formed in the same sidewall 72 that defines the radially inner surface of each of the viewing windows 30 (i.e., the surface defining the viewing windows 30 closest to the center of the stemless humeral component 10). Each of the undercuts 70 takes the form of a lip 74 that extends radially inwardly into its corresponding viewing window 30.

In such an arrangement, as will be discussed below in more detail, the lips 74 of the undercuts 70 are positioned to be engaged by a locking pawl of an implant insertion tool.

The stemless humeral component 10 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic stemless humeral component 10 may also be coated with a surface treatment, such as hydroxyapatite, to enhance biocompatibility. Moreover, the surfaces of the stemless humeral component 10 that engage the natural bone, such as the bottom surface 18 of the support flange 14, the outer surfaces of the elongated sleeve 36, and the legs 16, may be textured to facilitate securing the component to the bone. Such surfaces may also be porous coated to promote bone ingrowth for permanent fixation.

The stemless humeral component 10 and the head component 12 may be provided in various different configurations to provide the flexibility necessary to conform to varying anatomies from patient to patient. For example, the stemless humeral component 10 and the head component 12 may be provided in various diameters to match the needs of a given patient. It should be appreciated that the head thickness changes with the diameter of the head.

Referring now to FIGS. 6-24, there is shown a set of surgical instruments that may be used for the surgical preparation of the patient's humerus and the subsequent implantation of the stemless humeral component 10. The first of such instruments is an impaction handle 80 shown in FIGS. 6 and 7. As will be described below in more detail, the impaction handle 80 may be secured to a surgical punch or the stemless humeral component 10 to facilitate implantation of the stemless humeral component 10 into the patient's surgically-prepared humeral surface (i.e., the surface created by surgically resecting the humeral head). The impaction handle 80 includes an elongated body 82 having an impact head 84 on one end and an attachment mechanism 86 on its other end. A sleeve 88 is positioned around, and immovably coupled to, the outer surface of the impaction handle's body 82 such as by, for example, overmolding. The sleeve 88 functions as a grip for allowing the surgeon to hold the impaction handle 80 during a surgical procedure to implant the stemless humeral component 10.

The impact head 84 of the impaction handle 80 includes a circular metal plate 90 having an extraction flange 92 extending therefrom. In use, the surgeon holds the impaction handle 80 via the grip 88 and strikes the metal plate 90 with a surgical mallet, sledge, or other impaction tool to drive the surgical punch 240 (see FIG. 14) or the stemless humeral component 10 into the patient's surgically-prepared humeral surface.

The attachment mechanism 86 of the impaction handle 80 includes a lever 94 pivotally coupled to the impaction handle's body 82. The lever 94 includes a latching arm 96 and an actuation arm 98 extending at an angle from one end of the latching arm 96. A locking pawl 102 is positioned at an opposite end of the latching arm 96 and extends downwardly therefrom. The locking pawl 102 is configured to engage a lip or similar structure formed in one of the surgical instruments described herein (e.g., the surgical punch or the implant insertion tool) to selectively secure such instruments to the impaction handle 80. A connecting pin 104 is formed in the distal end of the impaction handle's body 82. The connecting pin 104 extends outwardly from an annular face 106 and has a cross section that substantially matches the shape of the corresponding opening defined in a number of the surgical instruments described herein (e.g., the surgical punch or the implant insertion tool). As shown in FIG. 6, the connecting pin 104 is substantially D-shaped in cross section and, as a result, includes a flat face 108.

The latching arm 96 of the lever 94 extends beyond the annular face 106 such that the locking pawl 102 is positioned over the connecting pin 104 and extends toward its flat face 108. This arrangement permits the locking pawl 102 to engage a lip or similar structure formed in a number of the surgical instruments described herein (e.g., the surgical punch or the implant insertion tool) to selectively secure such instruments to the impaction handle 80.

As shown in FIG. 7, a biasing element, such as spring 110 is coupled to the lever 94. The spring 110 biases the lever's locking pawl 102 toward the flat face 108 of the connecting pin 104. In doing so, the bias of the spring 110 locks the locking pawl 102, and hence the impaction handle 80, to a number of the surgical instruments described herein (e.g., the surgical punch or the implant insertion tool). When a surgeon or other user presses down on the lever's actuation arm 98, the bias exerted by the spring 110 is overcome, thereby causing the lever 94 to pivot. As the lever 94 is pivoted, the locking pawl 102 is moved in a direction away from the flat face 108 of the connecting pin 104. In such a way, the impaction handle 80 may be released from the surgical instrument to which it is coupled.

The metallic components of impaction handle 80 (e.g., the impact handle's body 82) may be constructed from a medical-grade metal such as stainless steel, cobalt chrome, or titanium, although other metals or alloys may be used. Moreover, in some embodiments, rigid polymers such as polyetheretherketone (PEEK) may also be used. The grip 88 may be constructed from a polymer such as silicone.

Referring now to FIGS. 8 and 9, there is shown an alignment handle 120. As will be described below in more detail, the alignment handle 120 may be secured to a sizing instrument or cutting guide during a procedure to implant the stemless humeral component 10 into the patient's surgically-prepared humeral surface (i.e., the surface created by surgically resecting the humeral head). The alignment handle 120 includes an elongated body 122 having an attachment mechanism 126 on its distal end. A sleeve 128 is positioned around, and immovably coupled to, the outer surface of the impaction handle's body 122 such as by, for example, overmolding. The sleeve 128 functions as a grip for allowing the surgeon to hold the alignment handle 120 during a surgical procedure to implant the stemless humeral component 10.

The attachment mechanism 126 of the alignment handle 120 is similar to the attachment mechanism 86 of the impaction handle 80 and, as such, includes a lever 134 pivotally coupled to the impaction handle's body 122. The lever 134 includes a latching arm 136 and an actuation arm 138 extending at an angle from one end of the latching arm 136. A locking pawl 142 is positioned at an opposite end of the latching arm 136 and extends downwardly therefrom. The locking pawl 142 is configured to engage a lip or similar structure formed in the sizing instrument 160 (see FIG. 10) to secure the sizing instrument 160 to the alignment handle 120. A keying pin 144 is formed in the distal end of the alignment handle's body 122. The keying pin 144 extends outwardly from an annular face 146 and has a cross section that substantially matches the shape of the corresponding key-hole shape opening 184 defined in the sizing instrument 160 (see FIG. 10). As shown in FIG. 8, the keying pin 144 is key-shaped in cross section and, as a result, includes a round portion having a rectangular portion secured thereto.

The latching arm 136 of the lever 134 extends beyond the annular face 146 such that the locking pawl 142 is positioned over the keying pin 144 and extends toward its upper surface. This arrangement permits the locking pawl 142 to engage a lip or similar structure formed in the sizing instrument 160 (see FIG. 10) to secure the sizing instrument 160 to the alignment handle 120.

As shown in FIG. 7, a biasing element, such as spring 150 is coupled to the lever 134. The spring 150 biases the lever's locking pawl 142 toward the upper surface of the keying pin 144. In doing so, the bias of the spring 150 locks the locking pawl 142, and hence the alignment handle 120, to the sizing instrument 160. When a surgeon or other user presses down on the lever's actuation arm 138, the bias exerted by the spring 150 is overcome, thereby causing the lever 134 to pivot. As the lever 134 is pivoted, the locking pawl 142 is moved in a direction away from the upper surface of the keying pin 144. In such a way, the alignment handle 120 may be released from the sizing instrument 160.

The metallic components of alignment handle 120 (e.g., the alignment handle's body 122) may be constructed from a medical-grade metal such as stainless steel, cobalt chrome, or titanium, although other metals or alloys may be used. Moreover, in some embodiments, rigid polymers such as polyetheretherketone (PEEK) may also be used. The grip 128 may be constructed from a polymer such as silicone.

Figure 11:
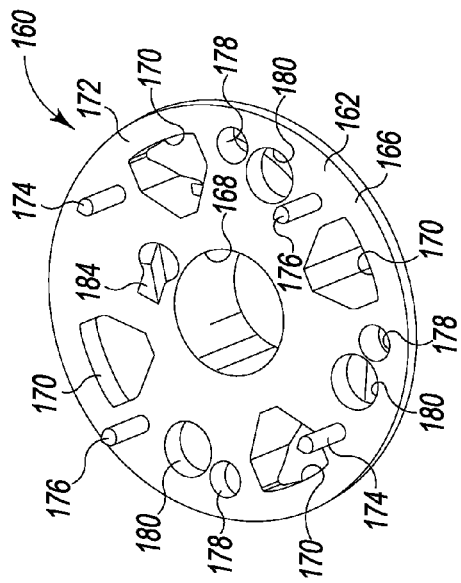
FIG. 11 is a lateral perspective view of the sizing component of FIG. 10.
Figure 10:
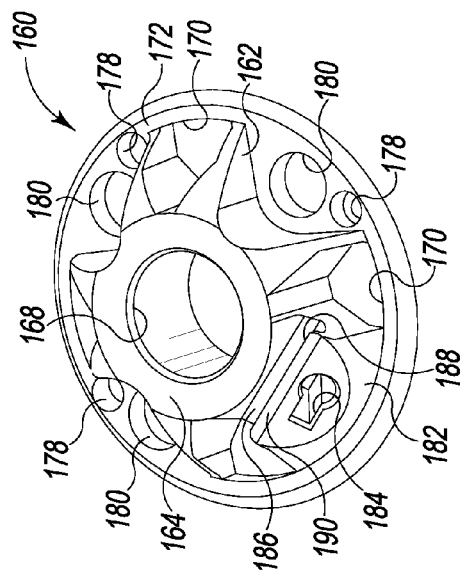
FIG. 10 is a medial perspective view of a sizing instrument that may be used in a surgical procedure to implant the stemless humeral component of FIG. 1.

Referring now to FIGS. 10 and 11, there is shown the sizing instrument 160. As will be described below in more detail, the sizing instrument 160 may be secured to the patient's surgically-prepared humeral surface during a procedure to implant the stemless humeral component 10 to function as both a sizing trial and a punch and drill guide.

The sizing instrument 160 includes a generally dome-shaped body 162 having flattened upper surface 164 and a substantially planar lower surface 166. An elongated bore 168 extends through the center of the sizing instrument 160 from its upper surface 164 to its lower surface 166. As will be described below in greater detail, the elongated bore 168 functions as a drill guide for drilling a hole in the patient's surgically-prepared humeral surface to receive the elongated sleeve 36 of the stemless humeral component 10 (see FIGS. 2 and 5).

The sizing instrument 160 also includes a number of generally triangular-shaped punch guide holes 170. As can be seen in FIG. 10, each of the punch guide holes 170 is located in one of the four quadrants of the sizing instrument's round flange 172. As such, each of the punch guide holes 170 is positioned about 90° from one another. As can be seen in FIGS. 2 and 4, the position of the punch guide holes 170 coincides with the position of the legs 16 of the stemless humeral component 10. As such, the holes 170 function as a punch guide for punching holes in the patient's surgically-prepared humeral surface to receive the legs 16 of the stemless humeral component 10 (see FIG. 29). To that end, the position of the punch guide holes 170 also coincides with the position of each of the tines 252 of the surgical punch 240 (see FIG. 14). As such, each of the tines 252 may be aligned with, and advanced through, one of the punch guide holes 170. In such a way, the sizing component 160 guides the surgeon's use of the surgical punch 240 while surgically preparing the patient's humeral surface to receive the legs 16 of the stemless humeral component 10 (see FIG. 29).

As can be seen in FIG. 11, the sizing instrument 160 has a number of spikes 174 extending downwardly from its lower surface 166. Each of the spikes 174 has a pointed distal tip 176. The spikes 174 are pressed or otherwise driven into the bone tissue of the patient's surgically-prepared humeral surface (i.e., the surface created by surgically resecting the humeral head) to secure the sizing instrument 160 in place during its use. A number of pin holes 178 are also formed in the sizing instrument's body 162 near its outer periphery. When a surgeon desires to supplement the attachment functionality of the spikes 174, surgical pins (not shown) may be inserted through the pin holes 178 to pin the sizing instrument 160 to the bone tissue of the patient's surgically-prepared humeral surface (i.e., the surface created by surgically resecting the humeral head).

Like the stemless humeral component 10, the sizing instrument's flange 172 also has a number of viewing windows 180 formed therein. The viewing windows 180 allow the surgeon to visualize the surgically-prepared humeral surface (i.e., the surface created by surgically resecting the humeral head) to ensure the sizing instrument 160 is fully seated during its use in the surgical procedure.

As can be seen in FIG. 10, the sizing instrument 160 has a connector 182 that may be engaged by the attachment mechanism 126 of the alignment handle 120 to secure the sizing instrument 160 to the alignment handle 120. The connector 182 has a key-hole shaped opening 184 formed therein. The key-hole opening 184 is sized and shaped to receive the keying pin 144 formed in the distal end of the alignment handle's body 122. The connector 182 also has a channel 186 formed therein. The connector 182 has an undercut 188 formed along the length of the channel 186. The undercut 188 takes the form of a lip 190 positioned at the top of the channel 186 and extending outwardly into the channel 186. The lip 190 is engaged by the locking pawl 142 of the alignment handle's attachment mechanism 126 (see FIGS. 8 and 9) to secure the sizing instrument 160 to the alignment handle 120.

As can be seen in FIG. 10, the connector 182 is confined within the sizing instrument's dome-shaped profile. As will be described below in greater detail, such an arrangement allows a trial humeral head to be installed on the sizing instrument without interference from the connector 182.

Like the other instruments and implants described herein, the sizing instrument 160 may be provided in a number of different sizes. For example, in the illustrative embodiment described herein, the sizing instrument 160 may be embodied in different diameters so as to mimic the various possible diameters of the stemless humeral component 10.

The sizing instrument 160 may be constructed from a medical-grade metal such as stainless steel, cobalt chrome, or titanium, although other metals or alloys may be used. Moreover, in some embodiments, rigid polymers such as polyetheretherketone (PEEK) may also be used. The polymers may be injection molded as well.

Figure 13:
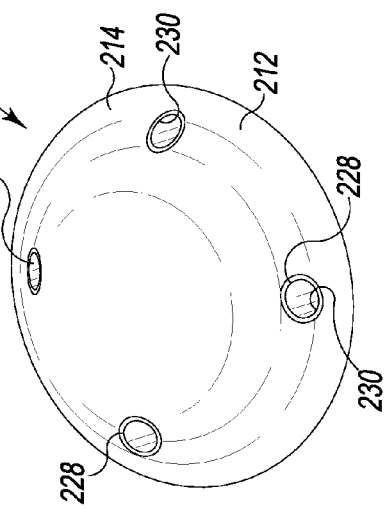
FIGS. 12 and 13 are perspective views of a trial head component that may be used in a surgical procedure to implant the stemless humeral component of FIG. 1.
Figure 12:
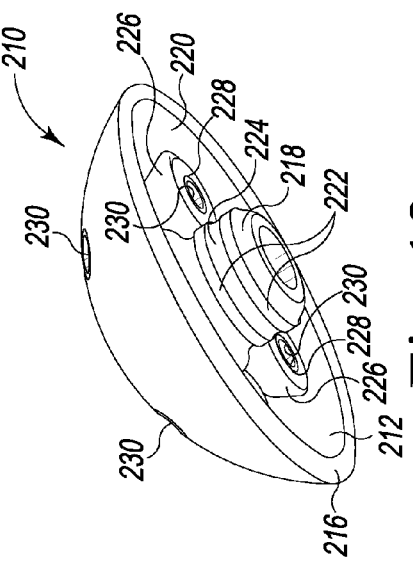

Referring now to FIGS. 12 and 13, there is shown a trial head component 210. The trial head component 210 is used for fit assessment during a surgical procedure to implant the stemless humeral component 10 and the humeral head component 12. In essence, the trial head component 210 is used to ensure proper size selection of the ultimate humeral head component 12 (i.e., the humeral head component 12 that is ultimately implanted in the patient's humerus). As will be discussed below in greater detail, the trial head component also functions as a drill guide for guiding a drill bit used to drill (or pre-drill) the holes in the patient's surgically-prepared humeral surface to receive the legs 16 of the stemless humeral component 10 (see FIGS. 31 and 32).

In the illustrative embodiment described herein, the trial head component 210 is embodied as a polymer trial instrument. As such, the trial head component 210 may be made of any suitable medical-grade polymeric material. Examples of such polymeric materials include polyethylene such as polyetheretherketone (PEEK) or acetal. In other embodiments, the trial head component may be formed from metal.

As a trial instrument for the humeral head component 12, the trial head component 210 includes a generally hemispherically-shaped body 212. As can be seen in FIG. 12, trial head component's body 212 includes a smooth, rounded, outer surface 214 that emanates from an annular rim 216 that defines the great circle of body's generally hemispherical shape. As can be seen in FIG. 12, the trial head component's body 212 is hollow. A center lug 218 extends downwardly from the center of the body's concave underside surface 220. The center lug 218 has a number of annular bands 222 formed in its outer surface 224. As will be described in greater detail, the trial head component 210 may be installed on the sizing instrument 160 or the stemless humeral component 10 by inserting the center lug 218 into the sizing instrument's elongated bore 168 or the stemless humeral component's tapered bore 40. The center lug's annular bands 222 frictionally engage the stemless humeral component's tapered bore 40 to frictionally secure the center lug, and hence the trial head component 210 to the stemless humeral component 10.

Figure 28:
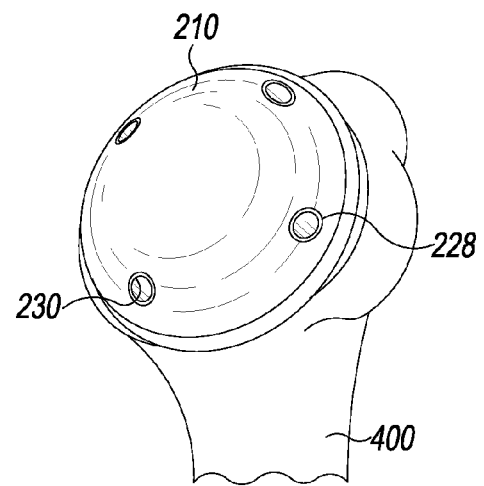
FIG. 28 is a perspective view showing the trial head component installed on the sizing instrument.

As can be seen in FIG. 12, the trial head component's body 212 also has a number of cylindrically-shaped bosses 226 extending downwardly from the center of the body's concave underside surface 220. Each of the bosses 226 has a cylindrically-shaped metallic sleeve 228 insert molded or otherwise positioned therein. The sleeves 228 have an elongated bore 230 formed therein, with such bores 230 extending throughout the entire length of the sleeves 228. The bores 230 function as drill guides for guiding a drill bit used to drill (or pre-drill) the holes in the patient's surgically-prepared humeral surface to receive the legs 16 of the stemless humeral component 10 (see FIGS. 31 and 32). As such, the position of each of the guide bores 230 coincides with, and is received into, the punch guide holes 170 of the sizing instrument 160 when the trial head component 210 is secured to the sizing instrument 160 (see FIG. 28). In particular, when the trial head component 210 is fully seated on the sizing instrument 160, the distal end of each of the bosses 226 formed in the trial head component 210 is received into a corresponding punch guide hole 170 of the sizing instrument 160 thereby aligning the guide bores 230 in the proper location.

Like the other instruments and implants described herein, the trial head component 210 may be provided in a number of different sizes. For example, in the illustrative embodiment described herein, the trial head component 210 may be embodied in different diameters (e.g., 15 mm, 18 mm, or 21 mm) so as to mimic a the diameter of the selected humeral head component 12.

Figure 14:
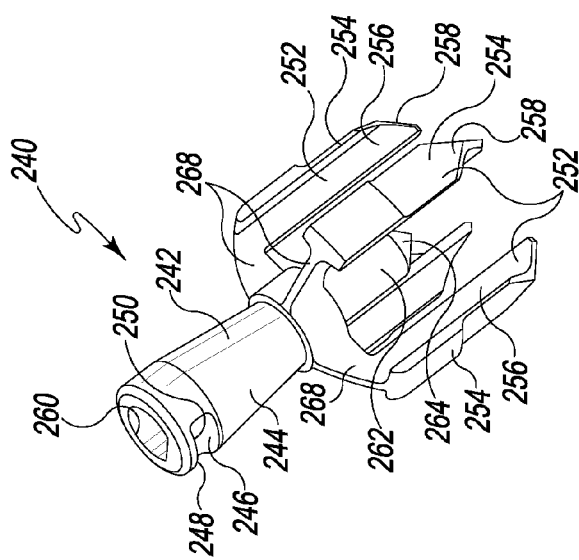
FIG. 14 is a perspective view of a surgical punch that may be used in a surgical procedure to implant the stemless humeral component of FIG. 1.
Figure 29:
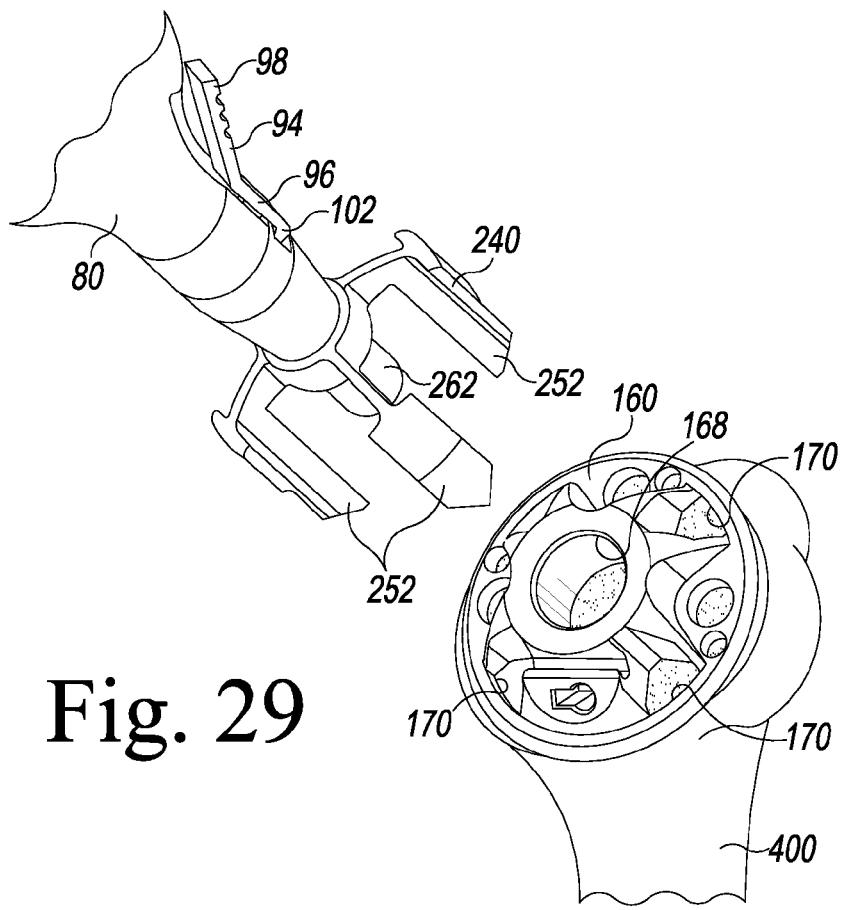
FIGS. 29 and 30 are perspective views showing the surgical punch being used to punch holes in the surgically-prepared surface of the patient's humerus.
Figure 30:
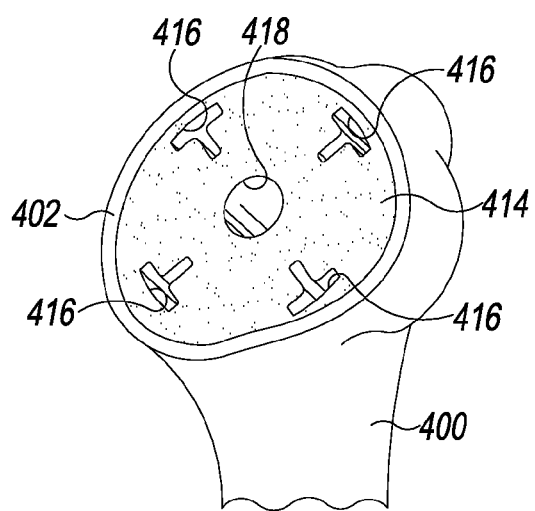

Referring now to FIG. 14, there is shown a surgical punch 240 that is used to punch holes in the patient's surgically-prepared humeral surface to receive the legs 16 of the stemless humeral component 10 (see FIGS. 29 and 30). Similarly to the other instruments described herein, the surgical punch 240 may be constructed from a medical-grade metal such as stainless steel, cobalt chrome, or titanium, although other metals or alloys may be used. Moreover, in some embodiments, rigid polymers such as polyetheretherketone (PEEK) may also be used.

The surgical punch 240 is generally fork-shaped and includes a metal body 242 that includes an attachment shaft 244. The proximal end of the attachment shaft 244 has a D-shaped socket 260 formed therein. The D-shaped socket 260 is sized, shaped, and positioned to receive the D-shaped connecting pin 104 of the attachment mechanism 86 of the impaction handle 80 (see FIG. 6). The outer surface of the attachment shaft 244 has a channel 246 formed therein. The sidewalls of the shaft 244 into which the channel 246 is formed define an undercut 248 that extends along the length of the channel 246. The undercut 248 takes the form of a lip 250 positioned at the top of the channel 246. When the impaction handle's connecting pin 104 is inserted in the D-shaped socket 260 of the surgical punch 240 and thereafter advanced downwardly, the lip 250 is engaged by the locking pawl 102 of the impaction handle's attachment mechanism 86 (see FIGS. 6 and 7) to secure the surgical punch 240 to the impaction handle 80.

At the end of the shaft 244 opposite the channel 246, the surgical punch's body 242 includes a number of tines 252. Each of the tines 252 is secured to the shaft 244 by a strut 268. The tines 252 function to punch holes in the patient's surgically-prepared humeral surface to receive the legs 16 of the stemless humeral component 10 (see FIGS. 29 and 30) and, as such, correspond in shape, size, and location with the legs 16 of the stemless humeral component 10. Like the legs 16 of the stemless humeral component 10, each of the surgical punch's tines 252 is generally T-shaped when viewed from a bottom elevation view (i.e., a view that is orthogonal to the longitudinal axis of the tine 252). In such an arrangement, each of the tines 252 has a bone-shaping plate 254 and an elongated rib 256. The elongated rib 256 extends along the length of the engaging plate 254 and, as such, forms the "trunk" of the T-shaped tine 252, with the engaging plate 254 forming the "cross bar" of the T-shaped tine 252. Specifically, the outer surface of the engaging plate 254 faces outwardly from the other tines (and hence the longitudinal axis of the surgical punch), with the rib 256 being secured to the backside of the tine's engaging plate 254 and extending inwardly in the direction toward the other tines 252. The longitudinal axis of the rib 256 is parallel with the longitudinal axis of the engaging plate 254. As can be seen in FIG. 14, each of the tines 252 includes a beveled distal end 258 that functions as a lead punch surface. The beveled distal end 258 also functions as a lead-in surface to facilitate insertion of the tine 252 into a pre-drilled hole in the patient's surgically-prepared humeral surface.

The position of the tines 252 coincides with the position of the punch guide holes 170 of the sizing instrument 160. As such, the punch guide holes 170 function to guide the advancement of the tines 252 to punch holes in the patient's surgically-prepared humeral surface to receive the legs 16 of the stemless humeral component 10 (see FIGS. 29 and 30). As such, each of the tines 252 may be aligned with, and advanced through, the punch guide holes 170.

The surgical punch's body 242 also includes a center spike 262 extending downwardly from the shaft 244 into the area between the tines 252. The center spike 262 is centered on the longitudinal axis of the surgical punch 240. The center spike 262 includes a pointed distal tip 264. The tip 264 of the center spike 262 makes a divot in the patient's surgically-prepared humeral surface during use of the surgical punch 240 to punch holes to receive the legs 16 of the stemless humeral component 10. Such a divot is positioned to receive the elongated sleeve 36 of the stemless humeral component 10.

Figure 16:
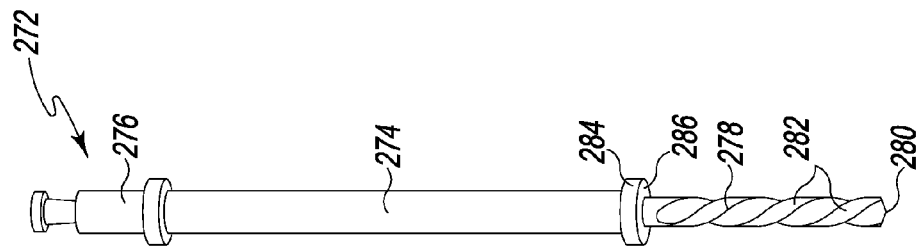
FIG. 16 is an elevational view of a peripheral drill that may be used in a surgical procedure to implant the stemless humeral component of FIG. 1.
Figure 15:
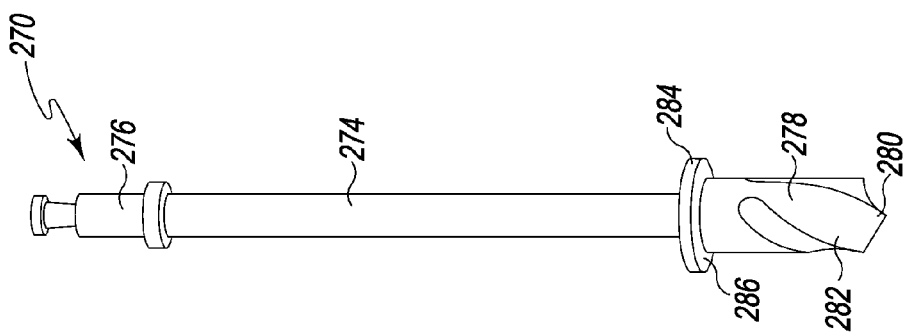
FIG. 15 is an elevational view of a center drill that may be used in a surgical procedure to implant the stemless humeral component of FIG. 1.

Referring now to FIGS. 15 and 16, there is shown a center drill bit 270 and a peripheral drill bit 272. The center drill bit 270 is used to surgically drill a hole in the patient's surgically-prepared humeral surface to receive the elongated sleeve 36 of the stemless humeral component 10. The peripheral drill bit 272, on the other hand, is used to drill (or pre-drill) the holes in the patient's surgically-prepared humeral surface to receive the legs 16 of the stemless humeral component 10 (see FIGS. 31 and 32). Each of the drill bits 270, 272 includes an elongated shank 274 having a proximal end 276 that fits into the chuck of a rotary power tool (not shown) or a manual handle (not shown). The drill bits 270, 272 also include a cutting head 278 located at the opposite, distal end of the shank 274. The cutting head 278 of the drill bits 270, 272 includes a sharp cutting tip 280 with a plurality of helical cutting flutes 282 extending therefrom.

Each of the drill bits 270, 272 also includes an annular collar 284 positioned above the cutting head 278 at the upper end of the cutting flutes 282. The collar 284 functions as a depth stop to ensure the drill bits 270, 272 drill their respective holes at the desired depths. In the case of the center drill bit 270, the collar has an outer diameter that is larger than the diameter of the elongated bore 168 of the sizing instrument 160. Hence, the center drill bit 270 may be advanced into the bone tissue until the lower surface 286 of the collar 284 bottoms out or otherwise engages the flattened upper surface 164 of the sizing instrument 160. Likewise, the peripheral drill bit 272 may be advanced into the bone tissue until the lower surface 286 of the collar 284 bottoms out or otherwise engages a rim or shelf within the sleeves 228 of the trial head component 210.

The drill bits 270, 272 may be constructed from a medical-grade metal such as stainless steel, cobalt chrome, or titanium, although other metals or alloys may be used. Moreover, in some embodiments, rigid polymers such as polyetheretherketone (PEEK) may also be used.

Figure 19:
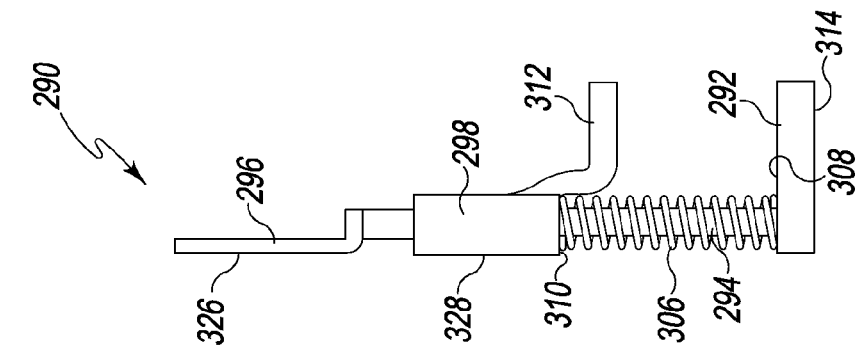
FIGS. 18 and 19 are side elevational views of the head resection guide of FIG. 17.
Figure 18:
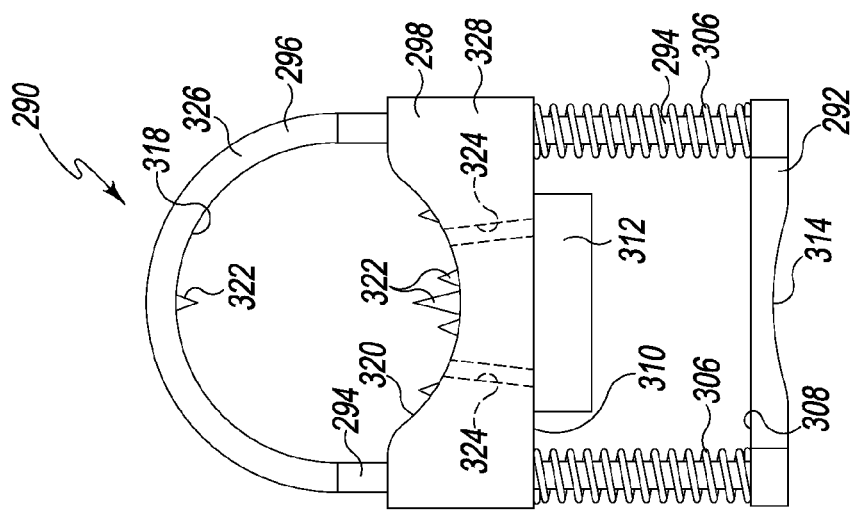
Figure 17:
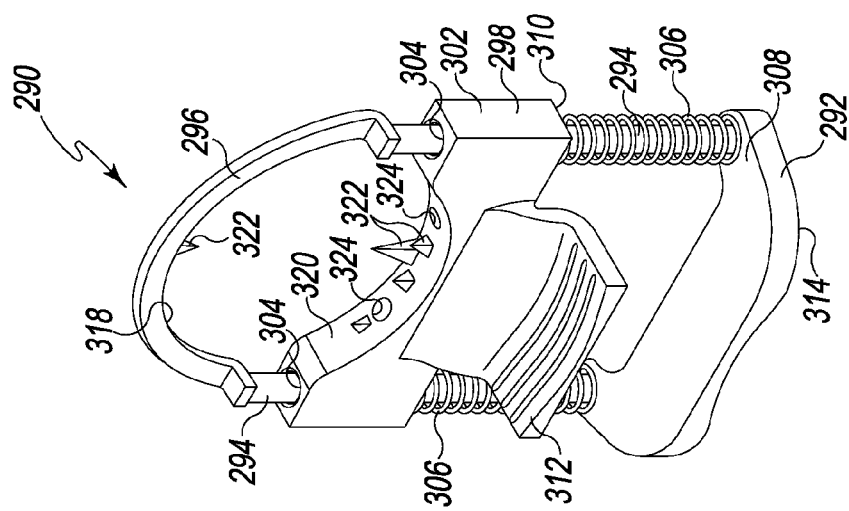
FIG. 17 is a perspective view of a head resection guide that may be used in a surgical procedure to implant the stemless humeral component of FIG. 1.

Referring now to FIGS. 17-19, there is shown a head resection guide 290. The head resection guide 290 is used as a cutting guide to guide the advancement of a bone saw blade to resect the humeral head of the patient. The head resection guide 290 includes a base 292 having a pair of rails 294 extending outwardly therefrom. An arcuate-shaped, stationary cutting guide 296 is secured to the end of the rails 296 opposite the base 292. Specifically, one end of the stationary cutting guide 296 is secured to one of the rails 294, with the other end of the stationary cutting guide 296 being secured to the other rail 294.

A movable cutting guide 298 is captured on the rails 294 and is movable back and forth along the rails 294. Specifically, the movable cutting guide 298 includes a guide body 302 having a pair of holes 304 formed therein. One of the guide rails 294 is positioned in one of the holes 304, with the other rail 294 being positioned in the other hole 304. As such, the movable cutting guide 298 may be moved along the rails 294 in a direction toward and away from the stationary cutting guide 296.

A biasing element, such as a coiled spring 306, is captured on each of the rails 294. The springs 306 are positioned between an upper surface 308 of the base 292 and the lower surface 310 of the movable cutting guide's body 302. As such, the springs 306 assert a spring bias on the movable cutting guide 298 so as to urge it in the direction toward the stationary cutting guide 296.

The movable cutting guide's body 302 also has a finger grip 312 formed therein. In the illustrative embodiment described herein, the finger grip 312 is embodied as a flange extending outwardly in a direction that is generally orthogonal to the rails 294. A surgeon or other user may grip the finger grip 312 and the lower surface 314 of the base 292 and thereafter squeeze his or her fingers. Doing so overcomes the spring bias of the springs 306 and urges or otherwise moves the movable cutting guide 298 in the direction away from the stationary cutting guide 296 (i.e., in a direction toward the base 292). Once the surgeon releases the finger grip 312, the spring bias of the springs 306 urges or otherwise moves the movable cutting guide 298 in the direction away back toward the stationary cutting guide 296 (i.e., in a direction away from the base 292).

As can be seen best in FIG. 18, both the stationary cutting guide 296 and the movable cutting guide 298 include rounded surfaces that cooperate to define a circular-shaped surface for capturing the patient's humeral head therein. Specifically, the stationary cutting guide 296 includes a rounded, generally semicircular-shaped posterior surface 318 that faces an rounded, generally semicircular-shaped anterior surface 320 of the movable cutting guide 298. As can be seen in FIGS. 17 and 18, a number of spikes 322 extend outwardly from each of the semicircular-shaped surfaces 318, 320 toward the opposite semicircular-shaped surface 318, 320. The spikes 322 engage the bone tissue of the patient's humerus to maintain the head resection guide 290 in a desired location and orientation during its use. As such, when a surgeon squeezes the finger grip 312 and the lower surface 314 of the base 292, the semicircular-shaped surfaces 318, 320 are moved away from one another thereby creating clearance to position the patient's humeral head between them. Thereafter, when the surgeon releases the finger grip 312 and the lower surface 314 of the base 292, the semicircular-shaped surfaces 318, 320 are toward one another thereby capturing the patient's humeral head therebetween with the spikes 322.

As can be seen in FIGS. 17 and 18, the movable cutting guide 298 has a number of pin holes 324 formed therein. The axis of each of the pin holes 324 extends in a direction that is oblique or angled relative to the rails 294 and the spikes 322. As will be discussed in more detail, surgical pins may be inserted through the pin holes 324 to pin the head resection guide 290 to the patient's humerus during resection of the patient's natural humeral head.

As can be seen best in the side view of FIG. 19, both the stationary cutting guide 296 and the movable cutting guide 298 include planar surfaces that cooperate to define a cutting guide surface for guiding a bone saw blade to resect the patient's natural humeral head. Specifically, the stationary cutting guide 296 includes a planar posterior guide surface 326 that aligns in a coplanar relationship with a planar anterior guide surface 328 of the movable cutting guide 298. Collectively, the two guide surfaces 326, 328 define a cutting surface upon which a bone saw blade may be supported (i.e., guided) during a cutting operation to resect the patient's natural humeral head. As can be seen in FIG. 19, the two guide surfaces 326, 328 lie in a plane that is generally parallel to the rails 294 and perpendicular to the finger grip 312 and the lower surface 314 of the base 292.

The head resection guide 290 may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIGS. 20-23, there is shown an implant insertion tool 330. The implant insertion tool 330 may be secured to the stemless humeral component 10 to facilitate implantation of the stemless humeral component 10 into the patient's surgically-prepared humeral surface. The implant insertion tool 330 includes an elongated body 332 that defines a cylindrically-shaped shaft 334 having a connector 336 on its proximal end. The connector 336 includes a D-shaped socket 338 formed in its proximal end. The D-shaped socket 338 is sized, shaped, and positioned to receive the D-shaped connecting pin 104 of the attachment mechanism 86 of the impaction handle 80 (see FIG. 6). The outer surface of the body's connector 336 has a channel 340 formed therein. The sidewalls of the connector 336 into which the channel 340 is formed define an undercut 342 that extends along the length of the channel 340. The undercut 342 takes the form of a lip 344 positioned at the top of the channel 340. When the impaction handle's connecting pin 104 is inserted in the D-shaped socket 338 of the implant insertion tool 330 and thereafter advanced downwardly, the lip 344 is engaged by the locking pawl 102 of the impaction handle's attachment mechanism 86 (see FIGS. 6 and 7) to secure the implant insertion tool 330 to the impaction handle 80.

The end of the of the implant insertion tool's body 332 opposite its connector 336 has an alignment flange 346 formed therein. The alignment flange 346 is embodied as an annular face having a number of protrusions or alignment keys 348 extending downwardly therefrom. The alignment keys 348 are sized, shaped, and positioned to be received into the viewing windows 30 formed in the stemless humeral component 10. The alignment flange 346 also has an alignment pin 350 extending downwardly from its annular face. The alignment pin 350 is sized, shaped, and positioned to be received into the tapered bore 40 formed in the stemless humeral component 10.

Figure 20:
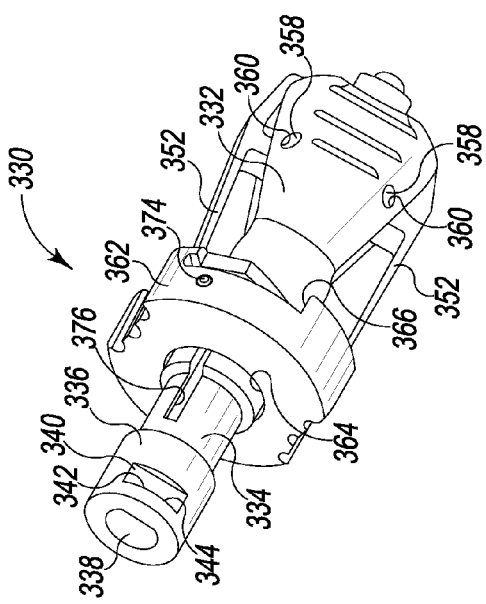
FIGS. 20 and 21 are perspective views of an implant insertion tool that may be used in a surgical procedure to implant the stemless humeral component of FIG. 1.
Figure 21:
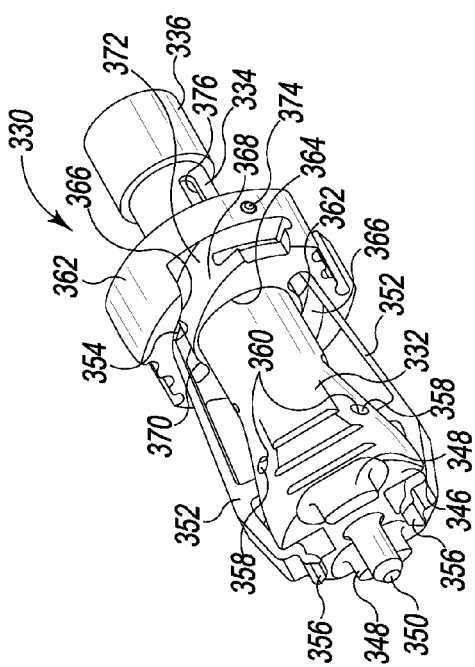
Figure 22:
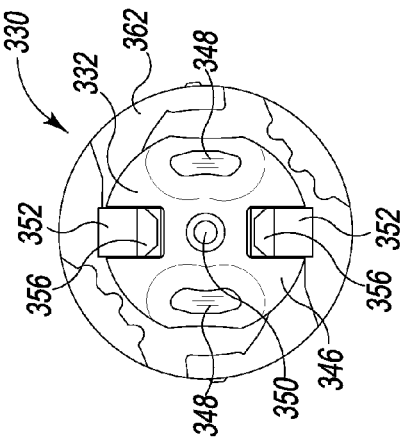
FIG. 22 is an end elevational view of the implant insertion tool of FIGS. 20 and 21 showing the implant insertion tool positioned in its unlocked position.
Figure 23:
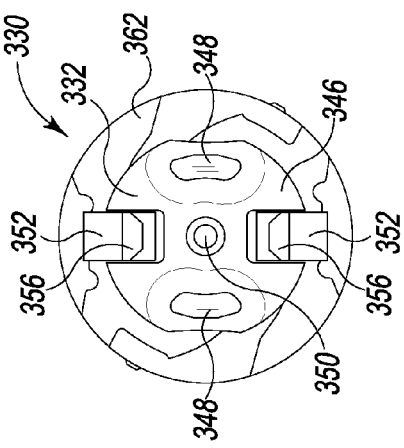
FIG. 23 is a view similar to FIG. 22, but showing the implant insertion tool positioned in its locked position.

As can be seen in FIGS. 20 and 21, a pair of locking arms 352 are pivotally coupled to the insertion tool's body 332. Each of the locking arms 352 has a cam follower 354 formed in its proximal end, and a generally L-shaped locking pawl 356 formed in its opposite, distal end. Each of the locking arms 352 is pivotally coupled to the implant insertion tool's body 332 at a location near its annular face 346 by a pivot pin 358 positioned in a bore 360 formed in the body 332. The locking arms 352 pivot about the pivot pins 358 such that movement of the cam followers 354 in the direction toward one another, and hence toward the shaft 334 of the insertion tool's body 332, causes movement of the locking pawls 356 in the direction away from one another, and hence away from the alignment pin 350 of the insertion tool's body 332. On the other hand, movement of the cam followers 354 in the direction away from one another, and hence away from the shaft 334 of the insertion tool's body 332, causes movement of the locking pawls 356 in the direction toward one another, and hence toward the alignment pin 350 of the insertion tool's body 332.

Such movement of the locking arms 352 may be used as part of a "quick connect" arrangement to selectively lock and release the stemless humeral component 10 from the implant insertion tool 330. In particular, when the insertion tool's alignment flange 346 is engaged with the stemless humeral component 10 such that its alignment pin 350 and alignment keys 348 are positioned in the stemless humeral component's tapered bore 40 and viewing windows 30, respectively, the locking pawls 356 of the locking arms 352 are positioned in the stemless humeral component's remaining viewing windows 30 (i.e., the viewing windows 30 not occupied by the alignment keys 348). So positioned, the locking pawls 356 may be moved into and out of engagement with the lips 74 of the undercuts 70 formed in the bottom surface 18 of the stemless humeral component's support flange 14 (see FIGS. 2 and 4). Specifically, the locking pawls 356 may be moved in the direction toward one another (i.e., toward the alignment pin 350 of the insertion tool's body 332) such that the locking pawls 356 engage the lips 74 of the undercuts 70 formed in the bottom surface 18 of the stemless humeral component's support flange 14 thereby securing the stemless humeral component 10 to the implant insertion tool 330. Oppositely, the locking pawls 356 may be moved in the direction away from one another (i.e., away from the alignment pin 350 of the insertion tool's body 332) such that the locking pawls 356 disengage the lips 74 of the undercuts 70 formed in the bottom surface 18 of the stemless humeral component's support flange 14 thereby releasing the stemless humeral component 10 from the implant insertion tool 330.

As can be seen in FIGS. 20 and 21, a rotating locking collar 362 is captured on the shaft 334 of the insertion tool's body 332. In particular, the locking collar 362 has a bore 364 extending through its center, with the shaft 334 of the insertion tool's body 332 being received (i.e., positioned) in the bore 364. As such, the locking collar 362 may be rotated both clockwise and counterclockwise about the shaft 334 of the insertion tool's body 332. As can be seen best in FIG. 20, the locking collar 362 has a pair of channels 366 formed in its underside. The cam followers 354 of the locking arms 352 ride in the channels 366 as the locking collar 362 is rotated about the shaft 334. The sidewall defining the inner side of the channels 366 defines a cam surface 368. As can be seen in FIG. 20, one end 370 of the cam surface 368 is nearer the locking collar's bore 364 (and hence the shaft 334 of the insertion tool's body 332) than the other end 372 of the cam surface 368. As such, as each of the cam followers 354 rides along its corresponding cam surface 368 in the direction from its inner end 370 to its outer end 372, the cam followers 354 move in the direction away from one another, and hence away from the shaft 334 of the insertion tool's body 332, thereby causing the locking arms 352 to pivot such that the locking pawls 356 are moved in a direction toward one another, and hence toward the alignment pin 350 of the insertion tool's body 332. As described above, such movement of the locking pawls 356 is used to lock the stemless humeral component 10 to the implant insertion tool 330. As can be seen in FIG. 20, in the illustrative embodiment described herein, clockwise rotation of the locking collar 362 causes the cam followers 354 to move along the cam surfaces 368 in such a direction (i.e., in a direction from the cam surface's inner end 370 to its outer end 372).

Oppositely, as each of the cam followers 354 rides along the corresponding cam surface 368 in the direction from its outer end 372 to its inner end 370, the cam followers 354 move in the direction toward one another, and hence toward the shaft 334 of the insertion tool's body 332, thereby causing the locking arms 352 to pivot such that the locking pawls 356 are moved in a direction away from one another, and hence away from the alignment pin 350 of the insertion tool's body 332. As described above, such movement of the locking pawls 356 is used to release the stemless humeral component 10 from the implant insertion tool 330. As can be seen in FIG. 20, in the illustrative embodiment described herein, counterclockwise rotation of the locking collar 362 causes the cam followers 354 to move along the cam surfaces 368 in such a direction (i.e., in a direction from the cam surface's outer end 372 to its inner end 370).

As can be seen in FIGS. 20 and 21, the locking collar 362 has a pair of guide pins 374 extending therethrough. The outer end of the guide pins 374 is positioned near the outer surface of the locking collar 362, with its inner end (not shown) positioned in an annular channel (not shown) formed on the outer surface of the shaft 334 of the insertion tool's body 332. The inner end of the guide pins 374 rides in such a channel during rotation of the locking collar 362. The shaft 334 of the insertion tool's body 332 also has a pair of linear channels 376 formed in its outer surface. The linear channels 376 are arranged parallel to both one another and the longitudinal axis of the shaft 334 of the insertion tool's body 332. When the inner ends of the guide pins 374 are aligned with, and received into, the linear channels 376, the locking collar 362 may be slid along the shaft 334 of the insertion tool's body 332 in the direction toward the connector 336 (i.e., away from the alignment flange 346). In doing so, each of the cam followers 352 of the locking arms 350 escape from their respective channels 366 of the locking collar 362. Such an arrangement allows the cam followers 352 and the channels 366 of the locking collar 362 to be fully exposed to cleaning fluid during cleaning of the implant insertion tool 330 between uses. The cam followers 352 may be slipped back into their respective channels 366 of the locking collar 362 by aligning them with the inner ends 370 of channels 366 as the locking collar 362 is slid along the shaft 334 of the insertion tool's body 332 in the direction away from the connector 336 (i.e., toward the alignment flange 346). Thereafter, the locking collar 362 may be rotated to recapture the cam followers 352 in their respective channels 366 of the locking collar 362.

The components of the implant insertion tool 330 (e.g., its body 332, locking arms 352, and locking collar 362) may be constructed from a medical-grade metal such as stainless steel, cobalt chrome, or titanium, although other metals or alloys may be used. Moreover, in some embodiments, rigid polymers such as polyetheretherketone (PEEK) may also be used.

Figure 24:
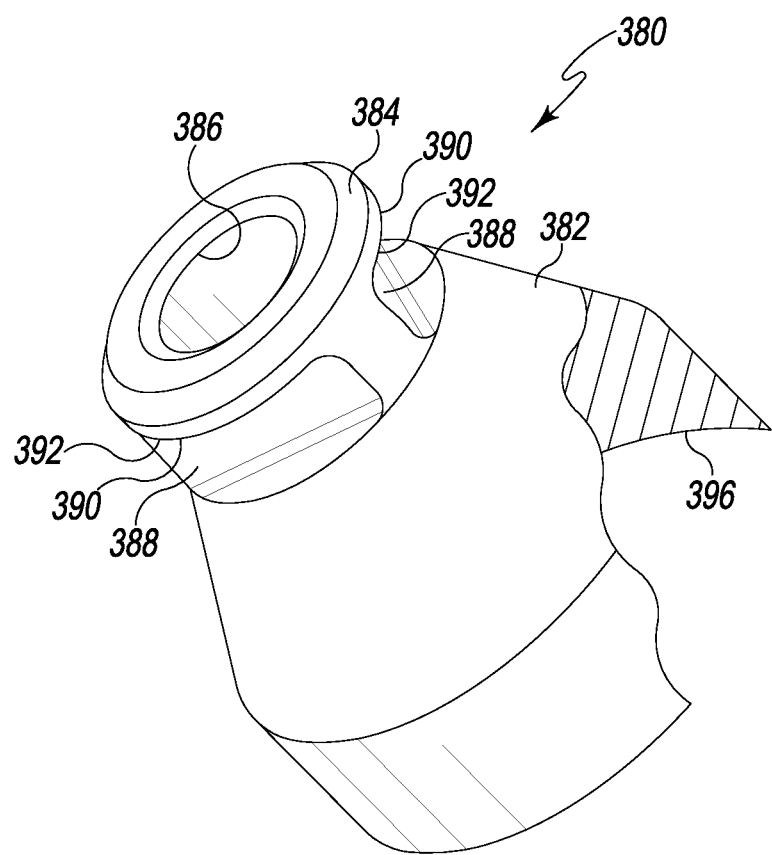
FIG. 24 is a fragmentary perspective view of a head impaction tool that may be used in a surgical procedure to implant the stemless humeral component of FIG. 1, note that a portion of the head impaction tool has been cut away for clarity of description.

Referring now to FIG. 24, there is shown an head impaction tool 380. The head impaction tool 380 may be used to impact, and hence taper lock, the head component 12 to the stemless humeral component 10. The head impaction tool 380 includes a generally conically-shaped body 382 having a connector 384 formed in its proximal end. The connector 384 includes a round opening 386 that is sized, shaped, and positioned to receive the connecting pin 104 of the attachment mechanism 86 of the impaction handle 80 (see FIG. 6). The connector 384 of the head impaction tool 380 also has three channels 388 formed therein. The sidewalls of the head impaction tool's body 382 into which the channels 388 are formed define undercuts 390 that extend along the length of the channels 388. Each of the undercuts 390 takes the form of a lip 392 positioned at the top of the respective channels 388. The lips 392 may be selectively engaged by the locking pawl 102 of the impaction handle's attachment mechanism 86 (see FIGS. 6 and 7) to secure head impaction tool 380 to the impaction handle 80.

The end of the head impaction tool's body 382 opposite the connector 384 has a rounded, concave impact surface 396 formed therein. The concave impact surface 396 is sized, shaped, and positioned to closely conform to the convex, nearly generally hemispherically-shaped outer surface of the head component 12. As will be described below in greater detail in regard to FIG. 35, when installing the head component 12 to the stemless humeral component 10, the head impaction tool 380 is first coupled to the impaction handle 80 and thereafter positioned such that the impact surface 396 of the head impaction tool 380 is placed in contact with the outer surface of the head component 12. The surgeon may then strike the impact handle's metal strike plate 90 with a surgical mallet, sledge, or other impaction tool to drive the head component 12 into taper lock attachment to the stemless humeral component 10. It should be appreciated that the head impaction tool 380 may be constructed from a polymer such as polyetheretherketone (PEEK), acetal, radel, or other polymer.

Referring now to FIGS. 25-36, there is shown a surgical procedure in which the various instruments described herein in regard to FIGS. 6-24 are used to surgically prepare the patient's humerus 400 for implantation of the stemless humeral prosthesis 10 of FIGS. 1-5. The surgical procedure begins with preoperative planning in which, amongst other things, a CT scan (2D or 3D) or other type of preoperative image (e.g., X-ray) may be obtained to plan the placement location and orientation of the stemless humeral component 10 and humeral head component. If the procedure being planned is a shoulder replacement procedure, the CT scan or other type of preoperative images will also be used to plan the placement location and orientation of a prosthetic glenoid component (not shown) to be implanted in the patient's glenoid. With the preoperative planning complete, the patient's soft tissue is dissected and retracted in order to allow access to the shoulder joint. Full (i.e., 360°) exposure of the patient's humeral head 402 is typically achieved.

Figure 25:
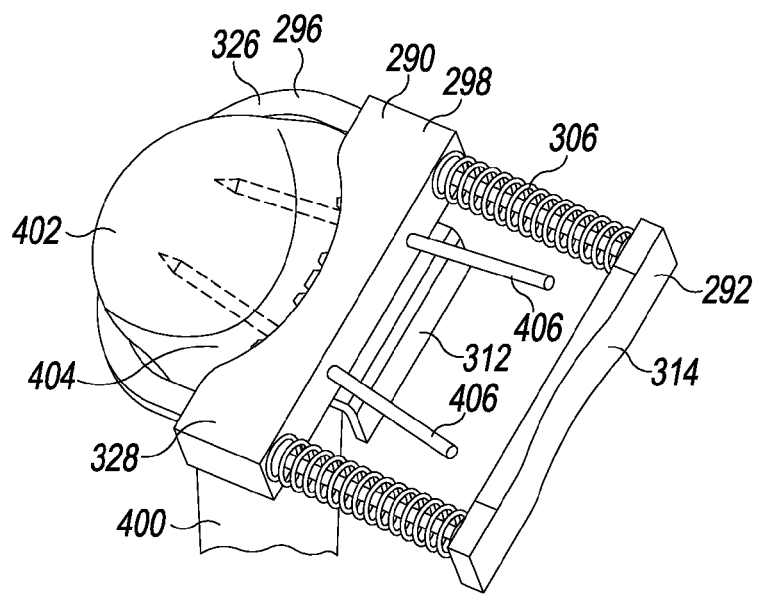
FIGS. 25 and 26 are perspective views showing the head resection guide being used to resect the humeral head of a patient's humerus.

Once the patient's humeral head 402 has been surgically exposed, the surgeon may then begin the process of resecting it. As shown in FIG. 25, the surgeon first installs the head resection guide 290 on the patient's humerus 400. To do so, the surgeon grips the finger grip 312 and the lower surface 314 of the head resection guide's base 292 and thereafter squeezes his or her fingers. Doing so overcomes the spring bias of the springs 306 and urges or otherwise moves the movable cutting guide 298 in the direction away from the stationary cutting guide 296 (i.e., in a direction toward the base 292) thereby creating clearance to position the patient's humeral head 402 between their respective semicircular-shaped surfaces 318, 320.

The surgeon then positions the head resection guide 290 around the patient's humeral head 402 such that the stationary cutting guide 296 rests on the posterior cuff insertion site of the patient's rotator cuff. Doing so protects the posterior rotator cuff during head resection and is a step in placing the guide 296 at the correct height and version. The surgeon then positions the anterior surface 320 of the movable cutting guide 298 against the anterior surface 404 of the patient's humerus 400 at the desired resection angle and height. The surgeon positions cutting guide 298 on the patient's humeral head 402 such that the anterior guide surface 328 is aligned with the articular margin of the humeral head 402. The surgeon then gently releases the finger grip 312 and the lower surface 314 of the base 292. In doing so, the respective semicircular-shaped surfaces 318, 320 of the movable cutting guide 298 and the stationary cutting guide 296 are moved toward one another thereby capturing the patient's humeral head 402 therebetween with the spikes 322.

Once the surgeon has placed the movable cutting guide 298 in the desired resection angle and height, the surgeon may insert a surgical pin 406 through each of the pin holes 324 to pin the head resection guide 290 to the patient's humerus 400 to maintain the anterior guide surface 328 of the movable cutting guide 298 in its desired position, as shown in FIG. 25.

Figure 26:
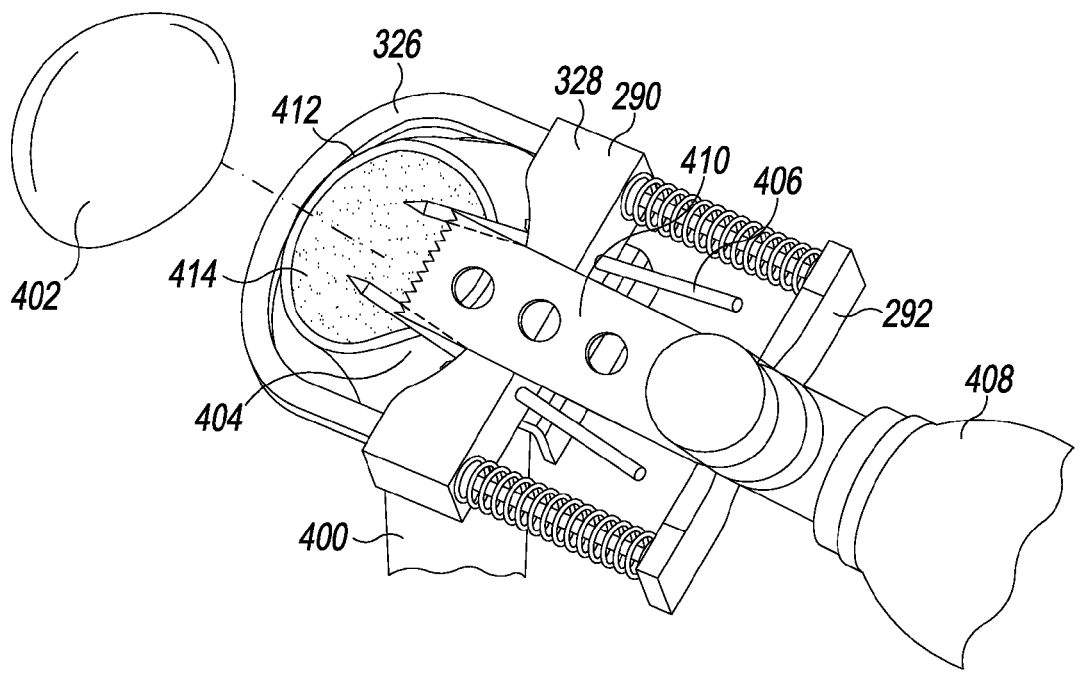

As shown in FIG. 26, the surgeon then operates a bone saw, such as an oscillating power saw 408, to resect the patient's humeral head 402. To do so, the surgeon positions the saw blade 410 of the power saw 408 on the planar anterior guide surface 328 of the movable cutting guide 298. The surgeon then actuates the oscillating power saw 408 and applies pressure on it so that it advances posteriorly and into contact with the anterior surface 404 of the patient's humerus 400. As the saw blade 410 is advanced posteriorly into contact with the anterior surface 404 of the humerus 400 and thereafter through its midsection in the direction toward its posterior surface 412, the oscillating motion of the bone saw 408 abrades the bone tissue of the humeral head 402.

The surgeon continues to posteriorly advance the power saw 408 until the saw blade 410 exits the bone. Specifically, the surgeon continues to operate the bone saw 408 until the distal tine of its blade 410 passes beyond the posterior surface 412 of the humeral head 402. Upon exit from the posterior surface 412 of the bone, the saw blade 410 is supported and guided by the posterior guide surface 326 of the stationary cutting guide 296. In such a way, the posterior guide surface 326 of the stationary cutting guide 296 prevents the saw blade 410 from contacting the patient's posterior rotator cuff. Once the saw blade 410 has exited the bone and advanced onto the posterior guide surface 326 of the stationary cutting guide 296, the surgeon may deactuate the bone saw 408 and thereafter then lift away the resected portion of the patient's humeral head 402. As can be seen in FIG. 26, the surgically resected surface 414 of the humerus 400 is substantially planar.

Figure 27:
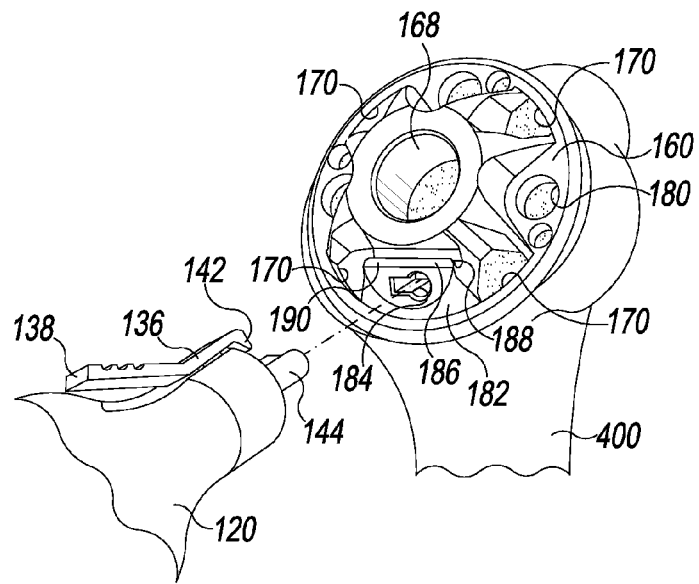
FIG. 27 is a perspective view showing the sizing instrument being installed on the patient's resected humeral head by use of the alignment handle.

As shown in FIG. 27, the surgeon now determines the appropriate size stemless humeral component 10 to implant on the surgically resected surface 414 of the humerus 400. To do so, the surgeon uses the sizing instrument 160. Specifically, as will now be described in more detail, the sizing instrument 160 may be secured to the patient's surgically resected surface 414 of the humerus 400 to function as both a sizing trial and a punch and drill guide. To do so, the surgeon selects an initial one of the differently-sized sizing instruments 160 that the surgeon estimates is the proper size for the patient. The surgeon then couples the selected sizing instrument 160 to the alignment handle 120. Specifically, the surgeon inserts and advances the keying pin 144 formed in the distal end of the alignment handle's body 122 into the key-hole shaped opening 184 formed in the sizing instrument 160 until the lip 190 of the sizing instrument's connector 182 is engaged by the locking pawl 142 of the alignment handle's attachment mechanism 126 (see FIGS. 8 and 9) thereby securing the sizing instrument 160 to the alignment handle 120. The surgeon then places the selected sizing instrument 160 onto the surgically resected surface 414 of the humerus 400 and assesses coverage. If the surgeon determines the selected sizing instrument 160 is not the proper size, the initial sizing instrument 160 is removed and a sizing instrument 160 having a different diameter is attached to the alignment handle 120 and assessed.

Once the sizing instrument 160 of the proper diameter has been determined, the surgeon secures the sizing instrument 160 to the surgically resected surface 414 of the humerus 400. To do so, the surgeon utilizes the alignment handle 120 to position the sizing instrument 160 in a desired location and orientation for the final implant (i.e., the stemless humeral component 10) with the spikes 174 of the sizing instrument 160 facing downwardly toward the surgically resected surface 414 of the humerus 400. The surgeon then presses or otherwise urges the sizing instrument 160 downwardly into the cancellous bone of the surgically-resected surface 414 of the humerus 400 thereby securing it in place as shown in FIG. 27. The surgeon may utilize the sizing instrument's viewing windows 180 to visualize the surgically-resected surface 414 of the humerus 400 to ensure the sizing instrument 160 is fully seated thereon.

Once the sizing instrument 160 has been installed on the surgically resected surface 414 of the humerus 400, the surgeon may then perform a pre-trial of the fit of the final humeral head component 12. To do so, the surgeon selects an initial one of the differently-sized trial head components 210 that the surgeon estimates is the proper size for the patient and thereafter installs the selected trial head component 210 to the sizing instrument 160 (see FIG. 28). The surgeon installs the trial head component 210 on the sizing instrument 160 by inserting its center lug 218 (see FIGS. 12 and 13) into the sizing instrument's elongated bore 168 and thereafter pressing or otherwise urging the trial head component 210 downwardly until it fully seats on the sizing instrument 160.

The trial head component 210 is used to ensure proper size selection of the ultimate humeral head component 12 (i.e., the humeral head component 12 that is ultimately implanted in the patient's humerus). As such, once the trial head component 210 is installed on the sizing instrument 160, the surgeon can visually assess its size and fit to get a sense of the size and fit of the final implant (i.e., the stemless humeral component 10 and the humeral head component 12). If the surgeon is not satisfied with the assessed size and fit, either one or both of the trial head component 210 and the sizing instrument 160 may be replaced. If the surgeon is satisfied with the assessed size and fit, the trial head component 210 is removed from the sizing instrument 160 and subsequent bone preparation of the patient's surgically resected humeral surface 414 is performed.

As shown in FIG. 29, the surgeon may then use the surgical punch 240 to punch holes in the patient's surgically-resected humeral surface 414 to receive the legs 16 and the elongated sleeve 36 of the stemless humeral component 10. It should be appreciated that the surgeon may utilize a number of fixation pins (not shown) inserted through the pin holes 178 to secure the sizing instrument 160 to the bone tissue of the patient's surgically-resected humeral surface 414 prior to use of the surgical punch 240. To perform the punching procedure, the surgeon first secures the surgical punch 240 to the impaction handle 80 by inserting the D-shaped connecting pin 104 into the D-shaped socket 260 formed in the attachment shaft 244 of the surgical punch 240 until the lip 250 formed in the attachment shaft 244 is engaged by the locking pawl 102 of the impaction handle's attachment mechanism 86 (see FIGS. 6 and 7) to secure the surgical punch 240 to the impaction handle 80.

Thereafter, the surgeon uses the impaction handle 80 to position the surgical punch 240 such that each of its tines 252 is aligned with one of the punch guide holes 170 of the sizing instrument 160. Doing so also aligns the surgical punch's center spike 262 with the elongated bore 168 of the sizing instrument 160. In such a way, the punch guide holes 170 and the elongated bore 168 function to guide the advancement of the tines 252 and the center spike 262, respectively.

Once the surgical punch 240 is positioned in the sizing instrument 160 in such a manner, the surgeon strikes the metal plate 90 of the impaction handle 80 with a surgical mallet, sledge, or other impaction tool to drive the surgical punch 240 into the patient's surgically-resected humeral surface 414 until the surgical punch bottoms out on the sizing instrument 160. As shown in FIG. 30, doing so creates a number of punched holes 416 in the patient's surgically-resected humeral surface 414 corresponding in shape, size, and location with the legs 16 of the stemless humeral component 12. As also shown in FIG. 30, impacting the surgical punch 240 in such a manner also creates a recess in the form of a divot 418 in the patient's surgically-resected humeral surface 414 corresponding in shape, size, and location to the elongated sleeve 36 of the stemless humeral component 10.

The surgeon then backs out the surgical punch 240 from the patient's surgically-resected humeral surface 414 to expose the surgically created holes 416 and divot 418, as shown in FIG. 30. If necessary, the surgeon may strike the underside of the impaction handle's extraction flange 92 to facilitate such extraction of the surgical punch 240.

Figure 31:
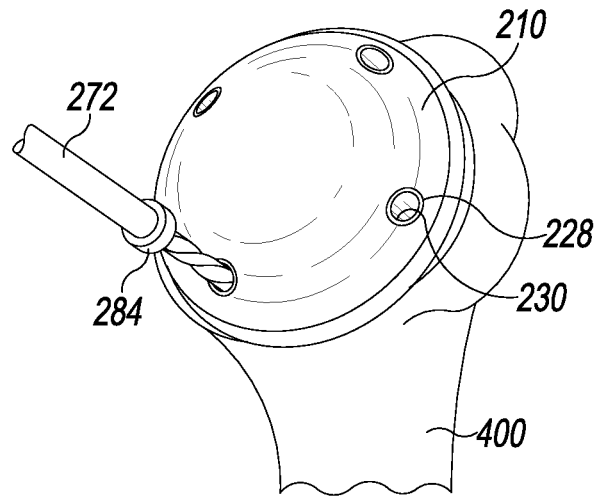
FIGS. 31 and 32 are perspective views showing the surgical drill being used to drill holes in the surgically-prepared surface of the patient's humerus.
Figure 32:
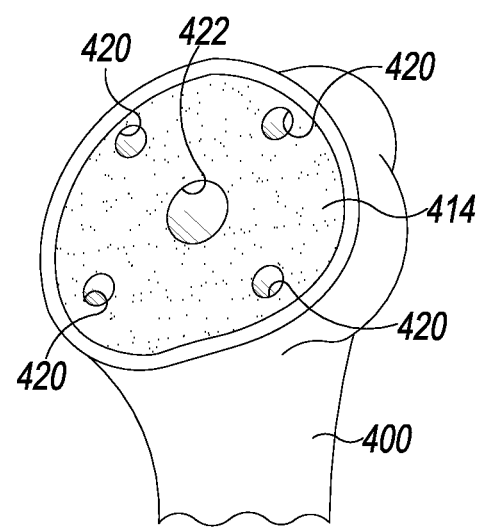

Referring now to FIGS. 31 and 32, there is shown a pre-conditioning procedure to the punching procedure described in regard to FIGS. 29 and 30. In other words, the drilling procedure may be performed as a pre-drilling procedure in which holes are pre-drilled in the patient's surgically-prepared humeral surface 414, with such pre-drilled holes then being punched by use of the surgical punch 240 in the manner described above to receive the legs 16 of the stemless humeral component 10. To perform such a drilling procedure, the surgeon utilizes the trial head component 210 with the installed sizing instrument 160. In bone preparation (as opposed to trialing), the trial head component 210 is used as a drill guide for guiding drill bits used to drill (or pre-drill) holes in the patient's surgically-prepared humeral surface 414 to receive the legs 16 and the elongated sleeve 36 of the stemless humeral component 10. To begin such a drilling procedure, the surgeon first selects the trial head component 210 corresponding in size to the installed sizing instrument 160 and thereafter installs the selected trial head component 210 to the sizing instrument 160 (see FIG. 31). The surgeon installs the trial head component 210 on the sizing instrument 160 by inserting its center lug 218 (see FIGS. 12 and 13) into the sizing instrument's elongated bore 168 and thereafter pressing or otherwise urging the trial head component 210 downwardly until it fully seats on the sizing instrument 160.

When the trial head component 210 is installed to the sizing instrument 160, the position of each of the trial head component's guide bores 230 coincides with, and is received into, the punch guide holes 170 of the sizing instrument 160. In particular, when the trial head component 210 is fully seated on the sizing instrument 160, the distal end of each of the bosses 226 formed in the trial head component 210 (see FIGS. 12 and 13) is received into a corresponding punch guide hole 170 of the sizing instrument 160 thereby aligning the guide bores 230 in the proper location.

The proximal end of the peripheral drill bit 272 is then inserted into the chuck of a rotary power tool (not shown) or a manual handle (not shown). The surgeon then inserts the tip 280 of the peripheral drill bit's cutting head 278 into one of the guide bores 230 of the trial head component 210 and actuates the power drill (or turns the manual handle). The surgeon advances the peripheral drill bit 272 into the bone tissue of the patient's surgically-resected humeral surface 414 until the lower surface 286 of the bit's collar 284 bottoms out or otherwise engages the rim or shelf in the sleeve 228 of the trial head component 210. The surgeon then removes the drill bit 272 from the guide bore 230 corresponding to the newly drilled peripheral hole and repeats the process in the remaining guide bores 230. The surgeon then removes the trial head component 210 from the sizing instrument 160 to expose the surgically-drilled peripheral holes 420 corresponding in location to where the legs 16 of the stemless humeral component 10 (see FIG. 32) will be implanted.

With the trial head component 210 removed, the surgeon then drills a hole in the patient's surgically-resected humeral surface 414 to receive the elongated sleeve 36 of the stemless humeral component 10. To do so, the surgeon secures the proximal end of the center drill bit 270 in the chuck of a rotary power tool (not shown) or a manual handle (not shown). The surgeon then inserts the tip 280 of the center drill bit's cutting head 278 into the elongated bore 168 of the sizing instrument 160 and actuates the power drill (or turns the manual handle). The surgeon advances the center drill bit 270 into the bone tissue of the patient's surgically-resected humeral surface 414 until the lower surface 286 of the bit's collar 284 bottoms out or otherwise engages the flattened upper surface 164 of the sizing instrument 160. The surgeon then removes the drill bit 270 from the elongated bore 168 of the sizing instrument 160.

As shown in FIG. 32, the surgeon then removes the sizing instrument 160 to expose the surgically-drilled peripheral holes 420 corresponding in location to where the legs 16 of the stemless humeral component 10 will be implanted, along with the surgically-drilled center hole 422 corresponding in location to where the elongated sleeve 36 of the stemless humeral component 10 will be implanted.

Once the patient's surgically-resected humeral surface 414 has been prepared, the surgeon may then implant the stemless humeral component 10. To do so, as shown in FIG. 33, the surgeon first secures the implant insertion tool 330 to the impaction handle 80 by inserting the handle's D-shaped connecting pin 104 into the D-shaped socket 338 of the implant insertion tool's connector 336 until the connector's lip 344 is engaged by the locking pawl 102 of the impaction handle's attachment mechanism 86 (see FIGS. 6 and 7) to secure the implant insertion tool 330 to the impaction handle 80.

Thereafter, the surgeon secures the appropriately sized stemless humeral component 10 (i.e., a component 10 having a diameter selected through trialing as described above) to the implant insertion tool 330. The surgeon first positions the locking collar 362 of the implant insertion tool 330 in an unlocked or release position in which the cam followers 354 of implant insertion tool's locking arms 352 are positioned near the inner end 370 of the locking collar's cam surface 368 thereby positioning the locking pawls 356 at their greatest distance away from one another. The surgeon then positions the insertion tool's alignment flange 346 in engagement with the stemless humeral component 10 such that its alignment pin 350 and alignment keys 348 are positioned in the stemless humeral component's tapered bore 40 and viewing windows 30, respectively. Doing so positions the locking pawls 356 of the implant insertion tool's locking arms 352 in the stemless humeral component's remaining viewing windows 30 (i.e., the viewing windows 30 not occupied by the alignment keys 348).

The surgeon rotates the locking collar 362 clockwise to move the locking collar 362 from its unlocked position to its locked position. Such rotation of the locking collar 362 causes each of the cam followers 354 of the implant insertion tool's locking arms 352 to ride along its corresponding cam surfaces 368 in the direction from its inner end 370 to its outer end 372. Doing so causes the cam followers 354 to move in the direction away from one another thereby causing the locking arms 352 to pivot such that the locking pawls 356 are moved in a direction toward one another. Such movement of the locking pawls 356 in the direction toward one another causes the locking pawls 356 to engage the lips 74 of the undercuts 70 formed in the bottom surface 18 of the stemless humeral component's support flange 14 thereby securing the stemless humeral component 10 to the implant insertion tool 330.

Figure 33:
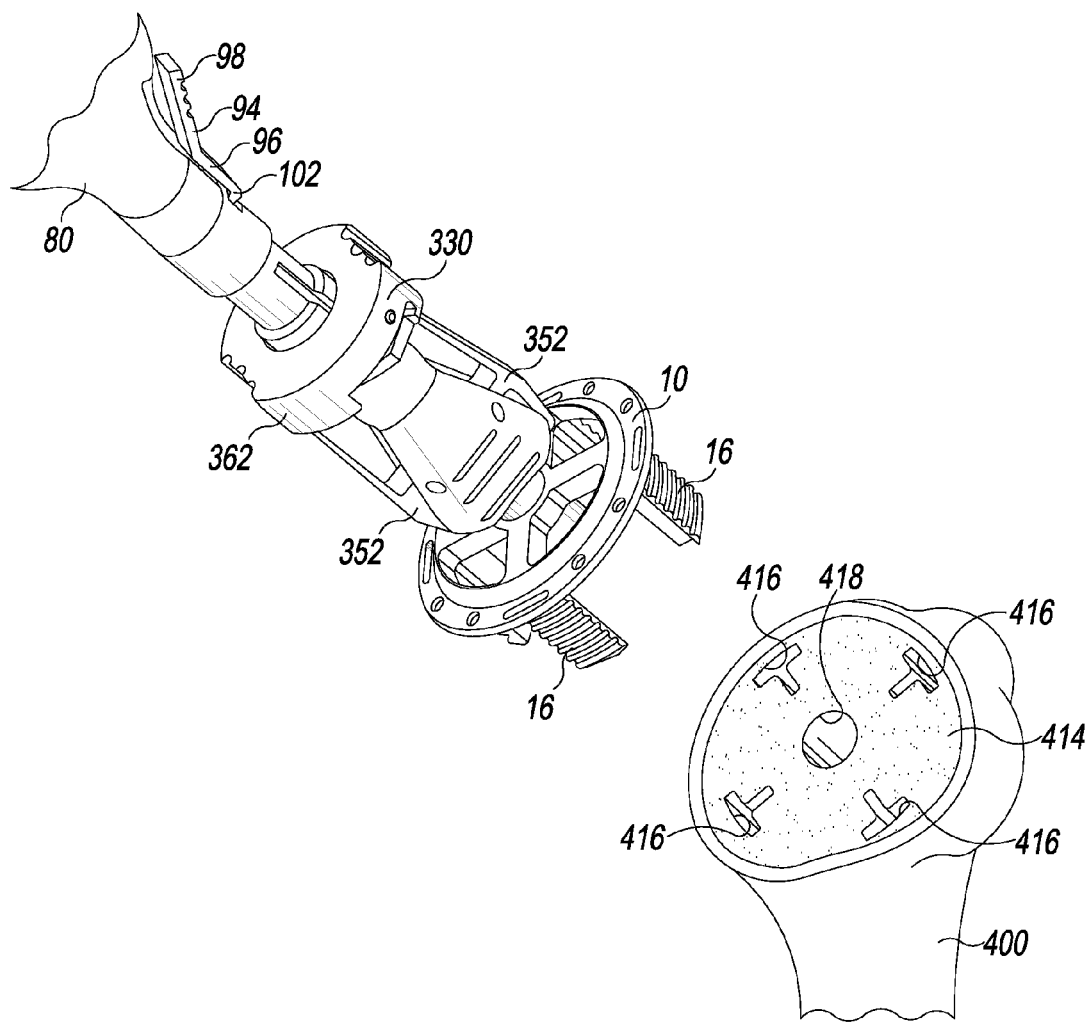
FIGS. 33 and 34 are perspective views showing the implant insertion tool being used to implant the stemless humeral component of FIG. 1 into the surgically-prepared surface of the patient's humerus.

Thereafter, as shown in FIG. 33, the surgeon uses the impaction handle 80 to position the stemless humeral component 10 such that each of its legs 16 is aligned with, and inserted into, one of the punched holes 416 formed in the patient's surgically-resected humeral surface 414. Doing so also aligns the elongated sleeve 36 of the stemless humeral component 10 with the divot 418/drilled hole 422 formed in the patient's surgically-resected humeral surface 414 (or the drilled center).

Once the stemless humeral component 10 is positioned in the punched holes 416 and the divot 418/drilled hole 422 in such a manner, the surgeon strikes the metal plate 90 of the impaction handle 80 with a surgical mallet, sledge, or other impaction tool to drive the stemless humeral component 10 into the bone tissue until the stemless humeral component 10 is fully seated on the patient's planar surgically-resected humeral surface 414. The surgeon may use the viewing windows 30 to visualize the surgically-resected humeral surface 414 to ensure the stemless humeral component 10 is fully seated thereon.

Figures 34, 35:
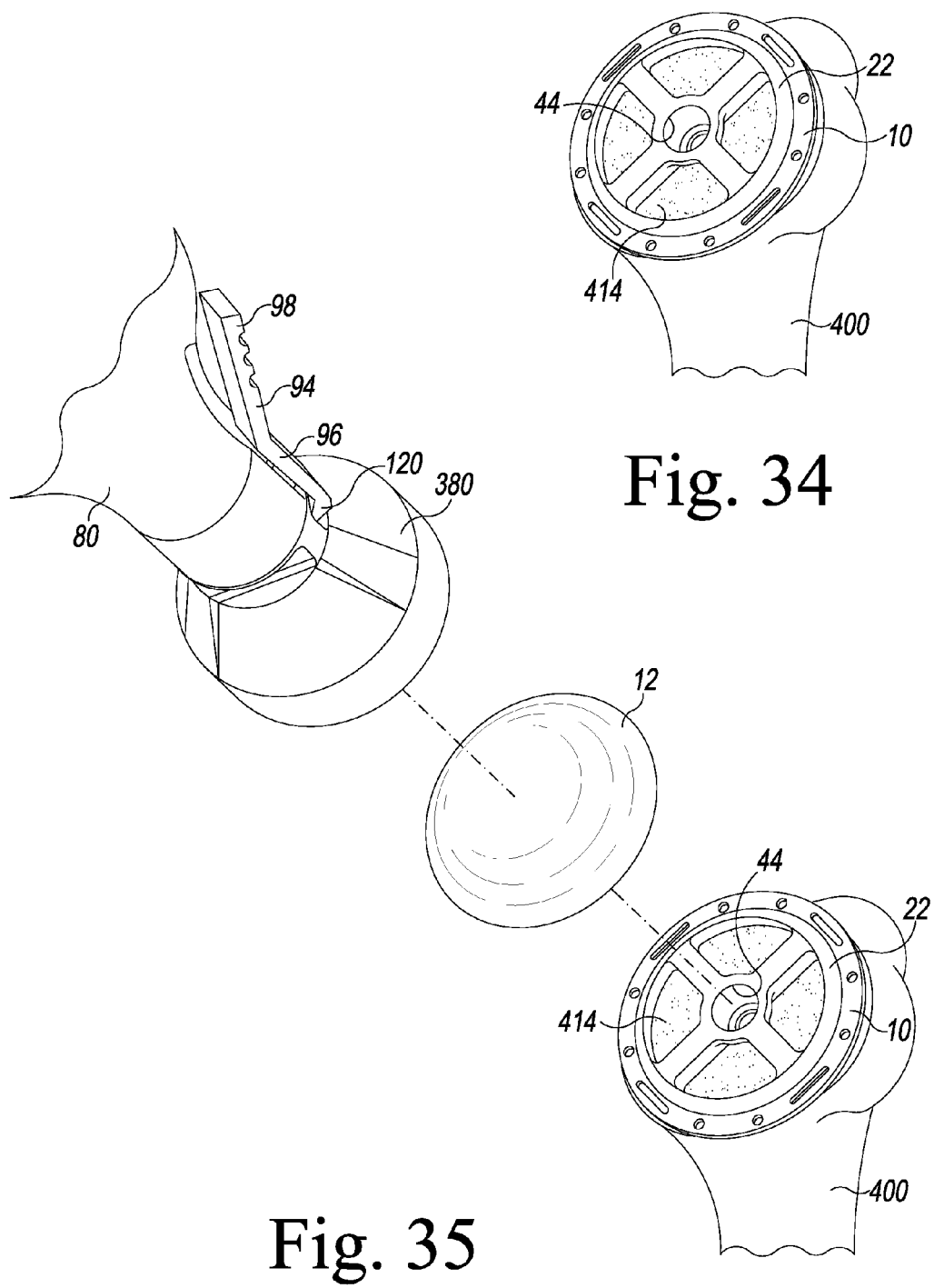
FIG. 35 is a perspective view showing the head impaction tool being used to install a head component to the implanted stemless humeral component.

The surgeon then releases the stemless humeral component 10 from the implant insertion tool 330. To do so, the surgeon rotates the locking collar 362 of the implant insertion tool 330 counterclockwise from its locked position to its unlocked position. Such rotation of the locking collar 362 causes each of the cam followers 354 of the implant insertion tool's locking arms 352 to ride along its corresponding cam surfaces 368 in the direction from its outer end 372 to its inner end 370. Doing so causes the cam followers 354 to move in the direction toward one another thereby causing the locking arms 352 to pivot such that the locking pawls 356 are moved in a direction away from one another. Such movement of the locking pawls 356 in the direction away from one another causes the locking pawls 356 to release the lips 74 of the undercuts 70 formed in the bottom surface 18 of the stemless humeral component's support flange 14 thereby releasing the stemless humeral component 10 from the implant insertion tool 330. As shown in FIG. 34, the surgeon then lifts the impaction handle 80, and hence the implant insertion tool 330, away thereby exposing the implanted stemless humeral component 10.

Once the stemless humeral component 10 has been implanted on the surgically resected surface 414 of the humerus 400, the surgeon may then perform a trial of the fit of the final humeral head component 12. To do so, the surgeon installs an appropriately sized trial head component 210 (i.e., the size selected during the earlier trialing steps) to the implanted stemless humeral component 10. The surgeon installs the trial head component 210 on implanted stemless humeral component 10 by inserting its center lug 218 (see FIGS. 12 and 13) into the tapered bore 40 of the implanted stemless humeral component 10 and thereafter pressing or otherwise urging the trial head component 210 downwardly until it fully seats on the implanted stemless humeral component 10. The center lug's annular bands 222 frictionally engage the sidewalls of the tapered bore 40 to frictionally secure the center lug, and hence the trial head component 210, to the implanted stemless humeral component 10. The surgeon then utilizes the trial head component 210 to assess coverage, soft tissue tension, and range of motion.

Once the surgeon is satisfied, the trial head component 210 is then removed and replaced with the ultimate humeral head component 12. In particular, as shown in FIG. 35, the surgeon then installs an appropriately sized humeral head component 12 (i.e., the size selected during the earlier trialing steps) to the implanted stemless humeral component 10. The surgeon installs the humeral head component 12 on implanted stemless humeral component 10 by inserting its tapered post 42 into the tapered bore 40 of the stemless humeral component's elongated sleeve 36 (see FIG. 36).

The head impaction tool 380 may be used to impact, and hence taper lock, the head component 12 to the stemless humeral component 10. To do so, as shown in FIG. 35, the surgeon first secures the head impaction tool 380 to the impaction handle 80 by inserting the handle's D-shaped connecting pin 104 into the round opening 386 of the head impaction tool's connector 384 until one of the connector's lip 392 is engaged by the locking pawl 102 of the impaction handle's attachment mechanism 86 (see FIGS. 6 and 7) to secure the head impaction tool 380 to the impaction handle 80.

Figure 36:
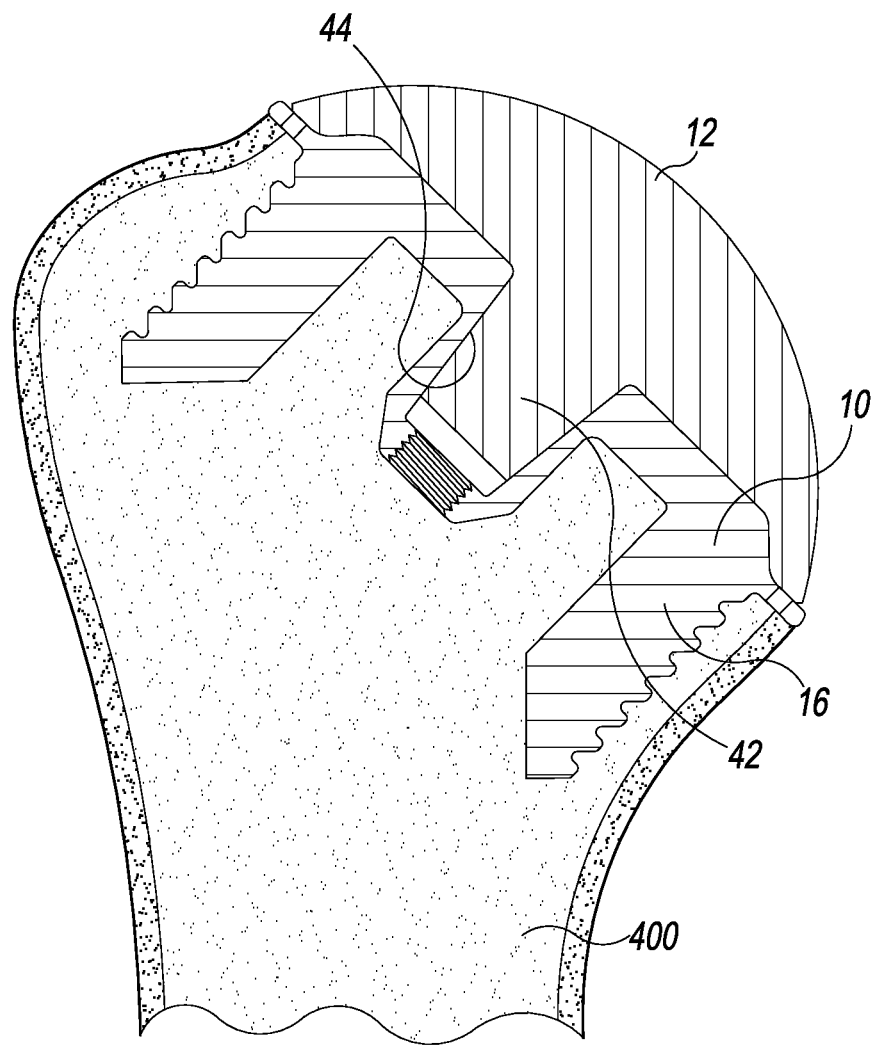
FIG. 36 is a fragmentary cross-sectional view showing the head component installed in the implanted stemless humeral component.

The surgeon then positions the impaction handle 80 that the head impaction tool's concave impact surface 396 is placed in contact with the generally hemispherically-shaped outer surface of the head component 12. The surgeon then strikes the impact handle's metal strike plate 90 with a surgical mallet, sledge, or other impaction tool to drive the humeral head component 12 downwardly so as to urge the tapered post 42 of the humeral head component 12 into contact with the sidewall defining the tapered bore 40 of the elongated sleeve 36 thereby taper locking the humeral head component 12 to the stemless humeral component 10. Such final assembly of the humeral head component 12 to the stemless humeral component 10 is shown in FIG. 36.

Figure 37:
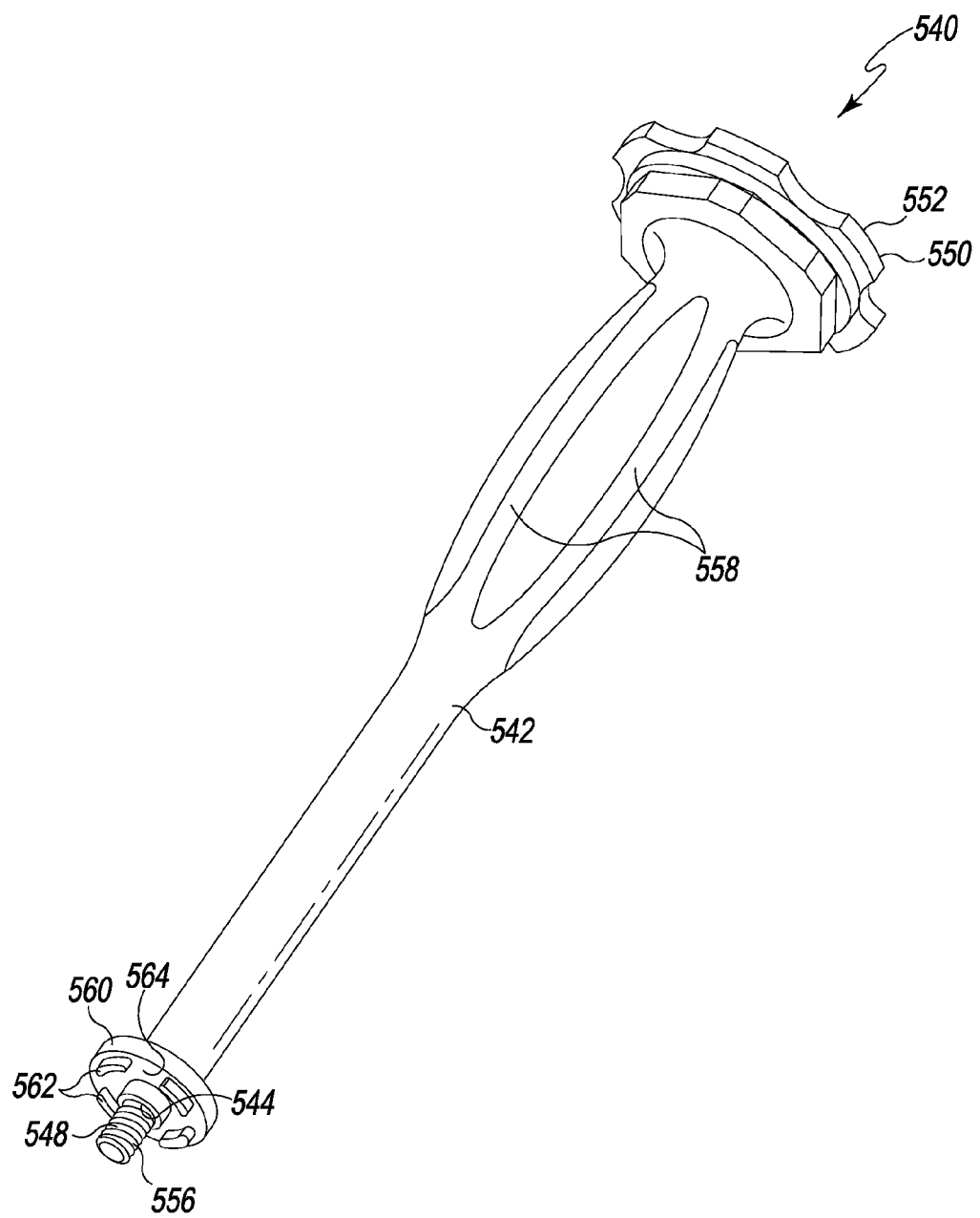
FIG. 37 is a perspective view of another implant insertion tool that may be used in a surgical procedure to implant the stemless humeral component of FIG. 1.

Referring now to FIG. 37, there is shown another embodiment of an implant insertion tool 540 that may be secured to the stemless humeral component 10 to facilitate implantation of the stemless humeral component 10 into the patient's surgically-prepared humeral surface 414. The implant insertion tool 540 includes a body 542 having an elongated bore 544 extending therethrough. A locking rod 548 is captured in the bore 544. In such an arrangement, the locking rod 548 rotates freely within the bore 544.

A knob 550 is secured to the proximal end of the locking rod 548. In addition to being used to secure the implant insertion tool 540 to the stemless humeral component 10, the knob 550 is also used as an impact surface. Namely, the surgeon strikes the upper surface 552 of the knob 550 to drive the stemless humeral component 10 into the bone tissue of the patient's surgically-prepared humeral surface 414.

The locking rod 548 has a set of locking threads 556 formed in its distal end (i.e., the end opposite the knob 550). The threads 556 are sized to be received into the complimentary threads 50 of the threaded bore 48 formed in the elongated sleeve 36 of the stemless humeral component 10. When a surgeon or other user rotates the knob 550, the locking screw's threads 556 are likewise rotated. Rotation in one direction (e.g., clockwise) may be used to tighten, and hence secure, the implant insertion tool 540 to the stemless humeral component 10, with rotation in the opposite direction (e.g., counterclockwise) being used to loosen, and hence, uncouple the implant insertion tool 540 from the stemless humeral component 10.

As can be seen in FIG. 37, a number of straight flutes or ridges 558 are formed in the end of the of the implant insertion tool's body 542 near the knob 550 of the locking rod 548. The ridges 558 function as a grip for allowing the surgeon to hold the implant insertion tool 540 during implantation of the stemless humeral component 10.

The end of the of the implant insertion tool's body 542 near the threads 556 of the locking rod 548 has an alignment collar 560 formed therein. The alignment collar 560 is embodied as an annular flange extending outwardly from the longitudinal axis of implant insertion tool's body 542. The alignment collar 560 has a number of protrusions or alignment keys 562 extending downwardly from its lower surface 564. As can be seen in FIG. 37, the alignment keys 562 are sized, shaped, and positioned to be received into the viewing windows 30 formed in the stemless humeral component 10.

With the alignment keys 562 positioned in the viewing windows 30, the stemless humeral component 10 is prevented from rotating relative the implant insertion tool 540 during rotation of the implant insertion tool's knob 550 thereby allowing the implant insertion tool's threads 556 to engage (or disengage) the stemless humeral component's threads 50.

In a manner similar to as described above in FIG. 33, the surgeon secures the stemless humeral implant 10 to the implant insertion tool 540 then uses the implant insertion tool 540 to align the stemless humeral component's legs 16 and elongated sleeve 36 to the punched holes 416 and the divot 418/drilled hole 422, respectively, formed in the surgically-resected humeral surface 414. Once the stemless humeral component 10 is positioned in the punched holes 416 and the divot 418/drilled hole 422 in such a manner, the surgeon strikes the upper surface 552 of the knob 550 with a surgical mallet, sledge, or other impaction tool to drive the stemless humeral component 10 into the bone tissue until the stemless humeral component 10 is fully seated on the patient's planar surgically-resected humeral surface 414. The surgeon may use the viewing windows 30 to visualize the surgically-resected humeral surface 414 to ensure the stemless humeral component 10 is fully seated thereon.

The components of the implant insertion tool 540 (i.e., its body 542 and the locking rod 548) may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIG. 38, there is shown another embodiment of an implant insertion tool 580. The implant insertion tool 580 may be secured to the stemless humeral component 10 to facilitate implantation of the stemless humeral component 10 into the patient's surgically-prepared humeral surface. The implant insertion tool 580 includes a body 582 having an elongated bore 584 extending therethrough. A locking rod such as a locking screw 588 is captured in the bore 584. In such an arrangement, the locking screw 588 rotates freely within the bore 584, but is prevented from being removed from the bore 584 (i.e., it is not removable from the implant insertion tool's body 582).

A D-shaped drive head 590 is formed in the proximal end of the locking screw 588, with a number of locking threads 592 being formed in its opposite, distal end. The threads 582 are sized to be received into the complimentary threads 50 of the threaded bore 48 formed in the elongated sleeve 36 of the stemless humeral component 10. The D-shaped drive head 590 is sized, shaped, and positioned to receive a D-shaped head of a ratchet or other surgical tool. As such, when the head of the racket is inserted in the implant insertion tool's drive head 590 and rotated, the locking screw's threads 592 are likewise rotated. Rotation in one direction (e.g., clockwise) may be used to tighten, and hence secure, the implant insertion tool 580 to the stemless humeral component 10, with rotation in the opposite direction (e.g., counterclockwise) being used to loosen, and hence, uncouple the implant insertion tool 580 from the stemless humeral component 10.

The end of the of the implant insertion tool's body 582 near the drive head 590 of the locking screw 588 has a channel 596 formed therein. The sidewalls of implant insertion tool's body 582 into which the channel 596 is formed define an undercut 598 that extends along the length of the channel 596. The undercut 598 takes the form of a lip 602 positioned at the top of the channel 596. The lip 602 is engaged by the locking pawl 102 of the impaction handle's attachment mechanism 86 (see FIGS. 6 and 7) to secure the implant insertion tool 580 to the impaction handle 80.

In a manner similar to as described above in FIG. 33, the surgeon secures the implant insertion tool 580 to the impaction handle 80 and thereafter secures the stemless humeral implant 10 to the implant insertion tool 580 or vice versa. The surgeon then uses the impaction handle 80 to align the stemless humeral component's legs 16 and elongated sleeve 36 to the punched holes 416 and the divot 418/drilled hole 422 formed in the surgically-resected humeral surface 414. Once the stemless humeral component 10 is positioned in the punched holes 416 and the divot 418/drilled hole 422 in such a manner, the surgeon strikes the metal plate 90 of the impaction handle 80 with a surgical mallet, sledge, or other impaction tool to drive the stemless humeral component 10 into the bone tissue until the stemless humeral component 10 is fully seated on the patient's planar surgically-resected humeral surface 414. The surgeon may use the viewing windows 30 to visualize the surgically-resected humeral surface 414 to ensure the stemless humeral component 10 is fully seated thereon.

The components of the implant insertion tool 580 (i.e., its body 582 and the locking screw 588) may be constructed from a medical-grade metal such as stainless steel, cobalt chrome, or titanium, although other metals or alloys may be used. Moreover, in some embodiments, rigid polymers such as polyetheretherketone (PEEK) may also be used. In other embodiments, the implant insertion tool 580 may be formed as a single monolithic component. In such embodiments, the implant insertion tool 580 may be threaded onto the implant or clipped onto the impaction handle for threading onto the implant. In other embodiments, the implant insertion tool 580 may include a connecting collar that surrounds the D-shaped drive socket. As such, the D-shaped drive socket 630 may be rotatable relative to the connecting collar.

Referring now to FIGS. 39 and 40, there is shown another embodiment of an implant insertion tool 620. The implant insertion tool 620 may be secured to the stemless humeral component 10 to facilitate implantation of the stemless humeral component 10 into the patient's surgically-prepared humeral surface 414. The implant insertion tool 620 includes a somewhat ring-shaped body 622 having an upper bore 624 extending through an upper portion of its body 622 and lower bore 626 extending through a lower portion of its body 622. The two bores 624, 626 are coaxial with one another (i.e., they share a common central axis). A locking rod 628 is captured in the bores 624, 626. In such an arrangement, the locking rod 628 rotates freely within the bores 624, 626, but is prevented from being removed from the bores 624, 626 (i.e., it is not removable from the implant insertion tool's body 622).

A D-shaped drive socket 630 is formed in the proximal end of the locking rod 628, with a number of locking threads 632 being formed in its opposite, distal end. The threads 632 are sized to be received into the complimentary threads 50 of the threaded bore 48 formed in the elongated sleeve 36 of the stemless humeral component 10 (see FIG. 5). The D-shaped drive socket 630 is sized, shaped, and positioned to receive the D-shaped connecting pin 104 of the attachment mechanism 86 of the impaction handle 80 (see FIG. 6).

As can be seen in FIGS. 39 and 40, the ring-shaped body 622 of the implant insertion tool 620 includes a connecting collar 634 that surrounds the D-shaped drive socket 630 of the locking rod 628. As such, the D-shaped drive socket 630 of the locking rod 628 is rotatable relative to the connecting collar 634 of the implant insertion tool's ring-shaped body 622. The outer surface of the connecting collar 634 has a number of ratchet slots 636 formed therein. One end 638 of the ratchet slots 636 is wider than its other end 640 thereby giving the ratchets slots 636 a generally L-shaped configuration. The sidewall 642 defining the narrow end 640 of the ratchet slots 636 defines a ramped-shaped or otherwise angled cam surface 644, whereas the sidewall 646 defining the wide end 638 of the ratchet slots 636 defines a vertical stop surface 648. When the impaction handle's connecting pin 104 is inserted in the implant insertion tool's D-shaped drive socket 630, the locking pawl 102 of the impaction handle's attachment mechanism 86 (see FIGS. 6 and 7) is positioned in one of the ratchet slots 636. The configuration of the ratchet slots 636 permits rotation of the impaction handle 80 (and hence the locking rod 628) relative to the ring-shaped body 622 of the implant insertion tool 620 in one direction (e.g., clockwise), but prevents rotation in the opposite direction (e.g., counterclockwise). In particular, rotation of the impaction handle 80 (and hence the locking rod 628) relative to the ring-shaped body 622 in the clockwise direction causes the leading edge of the locking pawl 102 of the impaction handle's attachment mechanism 86 (see FIGS. 6 and 7) to contact the ramped-shaped cam surface 644 that defines the narrow end 640 of the ratchet slot 636 in which the locking pawl 102 is captured. Continued clockwise rotation causes the locking pawl 102 to ride up the ramped-shaped cam surface 644 (as the spring bias of the spring impaction handle's 110 is overcome) and out of the ratchet slot 636. The locking pawl 102 rides on the outer surface of the connecting collar 634 between two adjacent ratchet slots 636 until the trailing edge of the locking pawl 102 clears the vertical stop surface 648 of the ratchet slot 636 adjacent to the one just exited by the locking pawl 102 at which point the spring bias of the spring impaction handle's 110 urges the locking pawl 102 downwardly into the ratchet slot 636.

Conversely, rotation of the impaction handle 80 (and hence the locking rod 628) relative to the ring-shaped body 622 in the counterclockwise direction causes the leading edge of the locking pawl 102 of the impaction handle's attachment mechanism 86 (see FIGS. 6 and 7) to contact the vertical stop surface 648 of the ratchet slot 636 that defines the wide end 638 of the ratchet slot 636 in which the locking pawl 102 is captured. Such contact with the vertical stop surface 648 prevents further rotation of the impaction handle 80 (and hence the locking rod 628) relative to the ring-shaped body 622 in the counterclockwise direction.

Such ratchet-type clockwise rotation of the impaction handle 80 (and hence the locking rod 628) relative to the ring-shaped body 622 is used to secure the stemless humeral component 10 to the implant insertion tool 620. In particular, when the impaction handle 80 is installed on the implant insertion tool 620 and rotated, the locking rod's threads 632 are likewise rotated. Rotation in one direction (e.g., clockwise) may be used to tighten, and hence secure, the implant insertion tool 580 to the stemless humeral component 10. Rotation in the opposite direction (e.g., counterclockwise) is used to loosen, and hence, uncouple the implant insertion tool 620 from the stemless humeral component 10. In order to perform such counterclockwise rotation, the surgeon presses and holds down on the actuation arm 98 of the impaction handle's lever 94 thereby lifting the impaction handle's locking pawl 102 out of the ratchets slots 636 of the implant insertion tool 620.

The end of the of the implant insertion tool's ring-shaped body 622 near the threads 632 of the locking rod 628 has an alignment collar 652 formed therein. The alignment collar 652 is embodied as an annular flange formed in the distal end 654 of the implant insertion tool's body 622. The alignment collar 652 has a number of protrusions or alignment keys 656 extending downwardly from its lower surface 658. As can be seen in FIG. 40, the alignment keys 656 are sized, shaped, and positioned to be received into the viewing windows 30 formed in the stemless humeral component 10. With the alignment keys 656 positioned in the viewing windows 30, the stemless humeral component 10 is prevented from rotating relative the implant insertion tool 620 during rotation of the implant insertion tool's locking rod 628 thereby allowing the implant insertion tool's threads 632 to engage (or disengage) the stemless humeral component's threads 50.

In a manner similar to as described above in FIG. 33, the surgeon secures the implant insertion tool 620 to the impaction handle 80 and thereafter secures the stemless humeral implant 10 to the implant insertion tool 620. The surgeon then uses the impaction handle 80 to align the stemless humeral component's legs 16 and elongated sleeve 36 to the punched holes 416 and the divot 418/drilled hole 422 formed in the surgically-resected humeral surface 414. Once the stemless humeral component 10 is positioned in the punched holes 416 and the divot 418 in such a manner, the surgeon strikes the metal plate 90 of the impaction handle 80 with a surgical mallet, sledge, or other impaction tool to drive the stemless humeral component 10 into the bone tissue until the stemless humeral component 10 is fully seated on the patient's planar surgically-resected humeral surface 414. The surgeon may use the viewing windows 30 to visualize the surgically-resected humeral surface 414 to ensure the stemless humeral component 10 is fully seated thereon.

The components of the implant insertion tool 620 (i.e., its body 622 and the locking rod 628) may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIGS. 41 and 42, there is shown another embodiment of an head resection guide 670 that may be used as a cutting guide to guide the advancement of a bone saw blade to resect the humeral head of the patient. Unlike the head resection guide 290 described above in regard to FIGS. 17-19, the head resection guide 670 is not adjustable, but rather is provided in a number of varying sizes (i.e., varying diameters) to fit the needs of a given patient. The head resection guide 670 includes a generally rectangular-shaped base 672 having a circular-shaped ring 674 secured thereto. The ring 674 extends outwardly from the base 672 and defines a circular-shaped opening 676. As will be described in more detail below, the patient's humeral head is captured in the opening 676 during resection thereof.

The head resection guide 670 has a connector 678 that may be engaged by the attachment mechanism 126 of the alignment handle 120 to secure the head resection guide 670 to the alignment handle 120. The connector 678 has a key-hole shaped opening 680 formed therein. The key-hole opening 680 is sized and shaped to receive the keying pin 144 formed in the distal end of the alignment handle's body 122. The connector 678 also has a channel 682 formed therein. An undercut 684 is formed along the length of the channel 682. The undercut 684 takes the form of a lip 686 positioned at the top of the channel 682 and extending outwardly into the channel 682. The lip 686 is engaged by the locking pawl 142 of the alignment handle's attachment mechanism 126 (see FIGS. 8 and 9) to secure the head resection guide 670 to the alignment handle 120.

The head resection guide's base 672 has a number of pin holes 692 formed therein. As will be discussed in more detail, surgical pins may be inserted through the pin holes 692 to pin the head resection guide 670 to the patient's humerus during resection of the patient's natural humeral head.

As can be seen in FIG. 42, both the base 672 and the ring 674 include planar surfaces that cooperate to define a cutting guide surface for guiding a bone saw blade to resect the patient's natural humeral head. Specifically, the base 672 includes a planar anterior guide surface 694 that aligns in a coplanar relationship with a planar posterior guide surface 696 of the ring 674. As described above, in the illustrative embodiment described herein, the head resection guide 670 is embodied as a monolithic structure. Hence, the two guide surfaces 694, 696 are embodied as a common surface that collectively defines a cutting surface upon which a bone saw blade may be supported (i.e., guided) during a cutting operation to resect the patient's natural humeral head.

In use, the surgeon installs the head resection guide 670 to the alignment handle 120 by inserting the keying pin 144 formed in the distal end of the alignment handle's body 122 into the key-hole opening 680 of the head resection guide's connector 678. In doing so, the connector's lip 686 is engaged by the locking pawl 142 of the alignment handle's attachment mechanism 126 (see FIGS. 8 and 9) thereby securing the head resection guide 670 to the alignment handle 120.

In a similar manner to as described above in regard to FIG. 26, the surgeon then uses the head resection guide 670 as a cutting guide to facilitate the surgical resection of the patient's humeral head 402. To do so, the surgeon uses the alignment handle 120 to position the head resection guide 670 around the patient's humeral head 402 such that the posterior section 702 of the ring 674 rests on the posterior cuff insertion site of the patient's rotator cuff. Doing so protects the posterior rotator cuff during head resection and acts as a step in placing the guide at the correct height and version. The surgeon then positions the anterior guide surface 694 of the base 672 relative to the anterior surface 404 of the patient's humerus 400 at the desired resection angle and height. The surgeon may then make any necessary minor adjustments to the positions of the anterior surface of the base relative to the anterior surface 404 and the anterior guide surface 694 relative to the articular margin to finalize the desired resection angle and height. Thereafter, the surgeon may insert a surgical pin 406 (see FIG. 26) through each of the pin holes 692 to pin the head resection guide 670 to the patient's humerus 400 to maintain the anterior guide surface 694 in its desired position. Once pinned in place, the surgeon disconnects the alignment handle 120 from the head resection guide 670.

Similar to as described in regard to FIG. 26, the surgeon then operates a bone saw, such as an oscillating power saw 408, to resect the patient's humeral head 402. To do so, the surgeon positions the saw blade 410 of the power saw 408 on the planar anterior guide surface 694 of the head resection guide's base 672. The surgeon then actuates the oscillating power saw 408 and applies pressure on it so that it advances posteriorly and into contact with the anterior surface 404 of the patient's humerus 400. As the saw blade 410 is advanced posteriorly into contact with the anterior surface 404 of the humerus 400 and thereafter through its midsection in the direction toward its posterior surface 412, the oscillating motion of the bone saw 408 abrades the bone tissue of the humeral head 402.

The surgeon continues to posteriorly advance the power saw 408 until the saw blade 410 exits the bone. Specifically, the surgeon continues to operate the bone saw 408 until the distal end of its blade 410 passes beyond the posterior surface 412 of the humeral head 402. Upon exit from the posterior surface 412 of the bone, the saw blade 410 is supported and guided by the posterior guide surface 696 of the ring 674. In such a way, the posterior guide surface 696 of the ring 674 prevents the saw blade 410 from contacting the patient's posterior rotator cuff. Once the saw blade 410 has exited the bone and advanced onto the posterior guide surface 696 of the ring 674, the surgeon may deactuate the bone saw 408 and thereafter then lift away the resected portion of the patient's humeral head 402.

The head resection guide 670 may be constructed from a medical-grade metal such as stainless steel, cobalt chrome, or titanium, although other metals or alloys may be used. Moreover, in some embodiments, rigid polymers such as polyetheretherketone (PEEK) may also be used.

Figure 43:
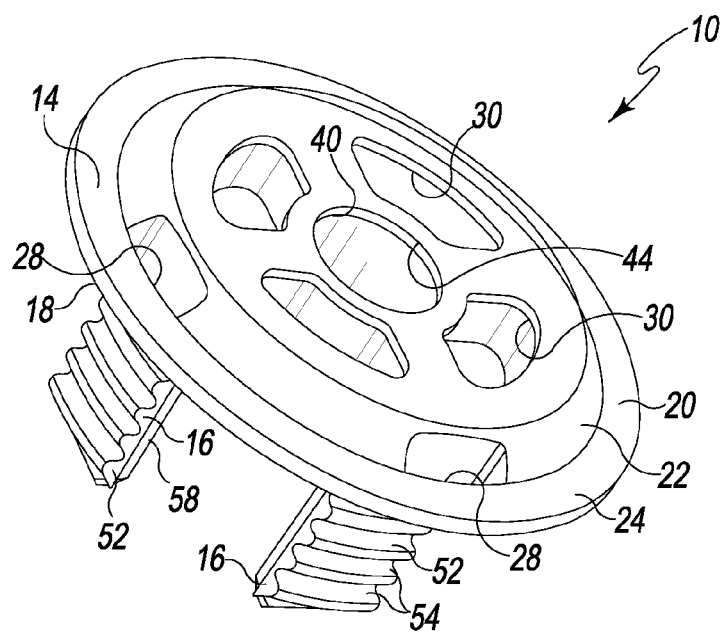
FIG. 43 is a medial perspective view of another embodiment of a stemless humeral component.
Figure 44:
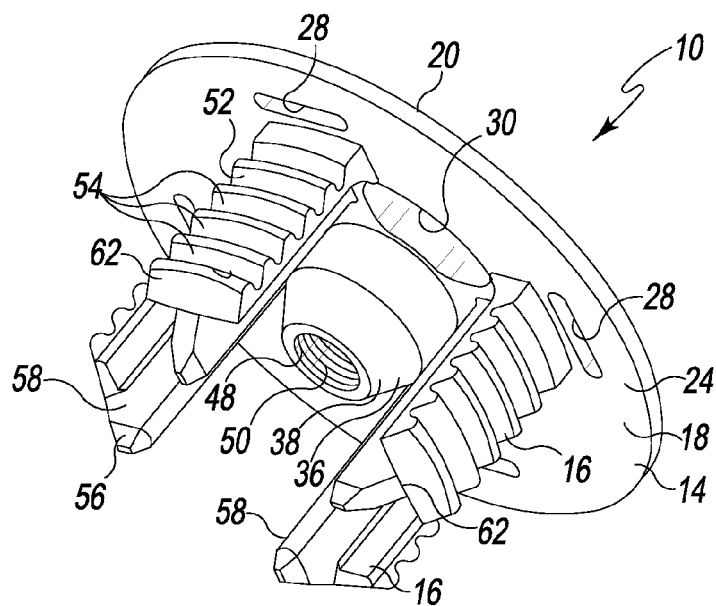
FIG. 44 is a lateral perspective view of the stemless humeral component of FIG. 43.

Referring now to FIGS. 43 and 44, there is shown another embodiment of the stemless humeral component 10. The features of the embodiment illustrated in FIGS. 43 and 44 are substantially similar to those discussed above in reference to the embodiment of FIGS. 1-5. Such features are designated in FIGS. 43 and 44 with the same reference numbers as those used in FIGS. 1-5. In essence, the embodiment of FIGS. 43 and 44 is substantially the same as the embodiment of FIGS. 1-5 with a few exceptions. For example, the suture holes 26 have been removed from the stemless humeral component of FIGS. 43 and 44. In such a case, the surgeon may use the viewing windows 30 in lieu of the removed suture holes 26 to suture bone wafers or soft tissue to the stemless humeral component 10. To accommodate such use of the viewing windows 30, the edges of the stemless humeral component's support flange 14 defining the viewing windows 30 may be rounded.

Figure 45:
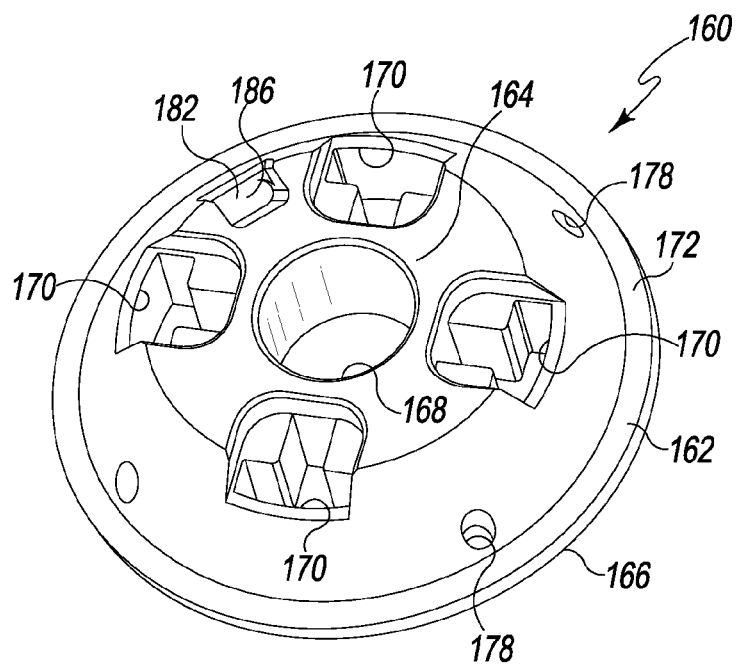
FIG. 45 is a medial perspective view of another embodiment of a sizing instrument that may be used in a surgical procedure to implant the stemless humeral component of FIG. 1.
Figure 46:
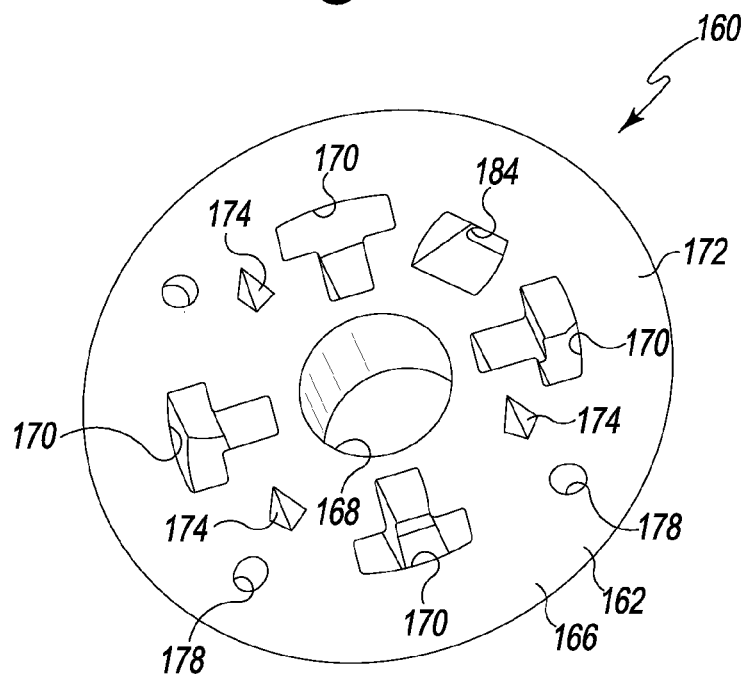
FIG. 46 is a lateral perspective view of the sizing component of FIG. 45.

Referring now to FIGS. 45 and 46, there is shown another embodiment of the sizing instrument 160. The features of the embodiment illustrated in FIGS. 45 and 46 are substantially similar to those discussed above in reference to the embodiment of FIGS. 10 and 11. Such features are designated in FIGS. 45 and 46 with the same reference numbers as those used in FIGS. 10 and 11. In essence, the embodiment of FIGS. 45 and 46 is substantially the same as the embodiment of FIGS. 10 and 11 with a few exceptions. For example, the viewing windows 180 have been removed from the sizing instrument 160 of FIGS. 45 and 46.

Moreover, the geometry of the punch guide holes 170 has been altered. In particular, the punch guide holes 170 are substantially T-shaped in the embodiment of the sizing instrument 160 shown in FIGS. 45 and 46. In such a way, the geometry of the punch guide holes 170 more closely corresponds with the geometry of the T-shaped tines 252 of the surgical punch 240.

In addition, the geometry of the connector 182 has been altered in the embodiment of the sizing instrument 160 shown in FIGS. 45 and 46. To accommodate such a change, the attachment mechanism 126 of the alignment handle 120 may also be altered to secure the sizing instrument 160 thereto.

Figure 47:
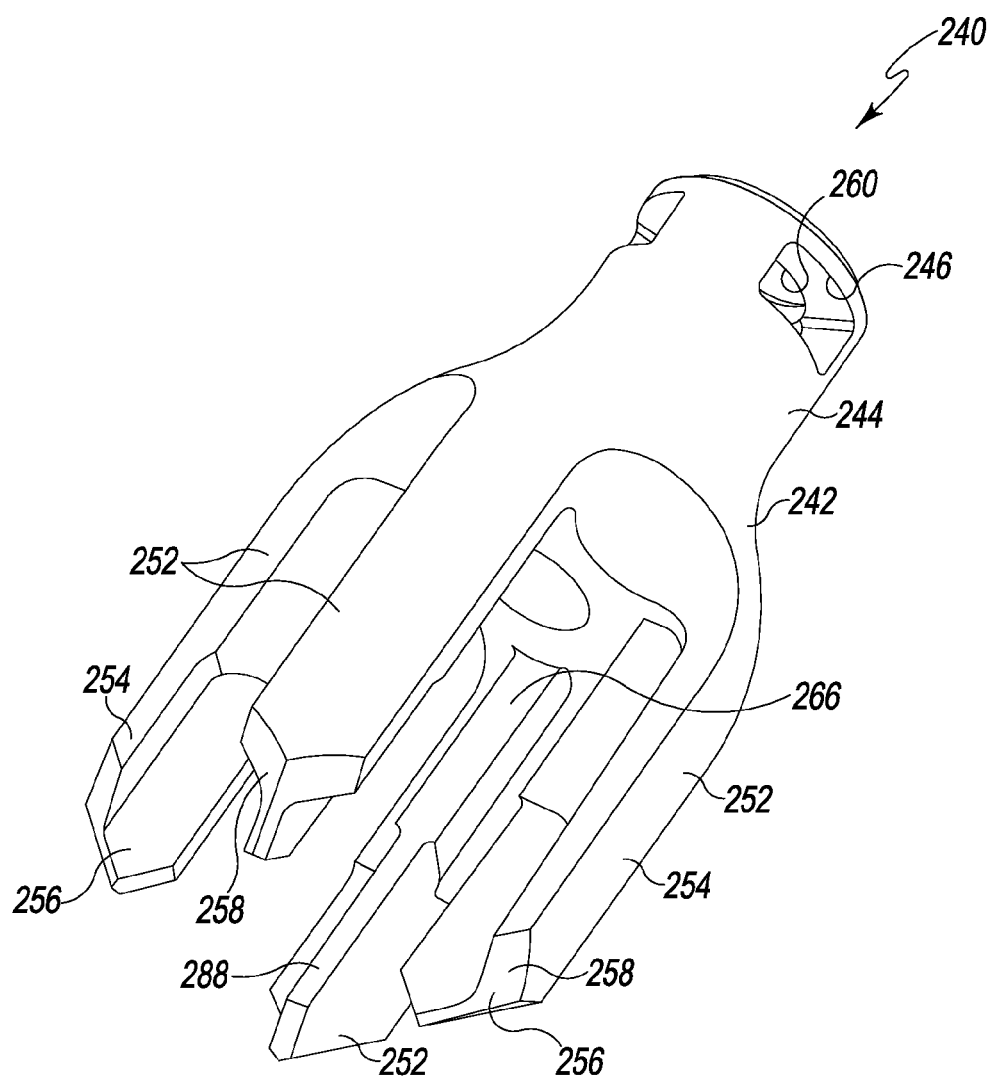
FIG. 47 is a perspective view of another embodiment of a surgical punch that may be used in a surgical procedure to implant the stemless humeral component of FIG. 1.

Referring now to FIG. 47, there is shown another embodiment of the surgical punch 240. The features of the embodiment illustrated in FIG. 47 are substantially similar to those discussed above in reference to the embodiment of FIG. 14. Such features are designated in FIG. 47 with the same reference numbers as those used in FIG. 14. In essence, the embodiment of FIG. 47 is substantially the same as the embodiment of FIG. 14 with a few exceptions. For example, the center spike 262 has been removed from the surgical punch 240 of FIG. 47. In such a case, the surgeon may use the center drill 270 to drill a hole in the patient's surgically-prepared humerus to accommodate the elongated sleeve 36 of the stemless humeral component 10 in the manner discussed above.

Moreover, the struts 268 have been removed such that the tines 252 are more integrally formed in the surgical punch's body 242. In addition, the geometry of the surgical punch's connecting socket 260 and connecting channel 246 have been altered in the embodiment of the surgical punch 240 shown in FIG. 47. To accommodate such a change, the attachment mechanism 86 of the impact handle 80 may also be altered to secure the surgical punch 240 thereto.

Moreover, as can be seen in FIG. 47, the proximal end 266 of each of the ribs 256 of the tines 252 (i.e., the end secured to the punch's shaft 244) is wider than the opposite, distal end 288 of each rib 256. As such, the corresponding shape of the punched holes formed in the patient's surgically-prepared humerus is wider at its open end than at its blind end. Such a widened opening facilitates insertion of the cantilevered legs 16 of the stemless humeral component 10.

Figure 48:
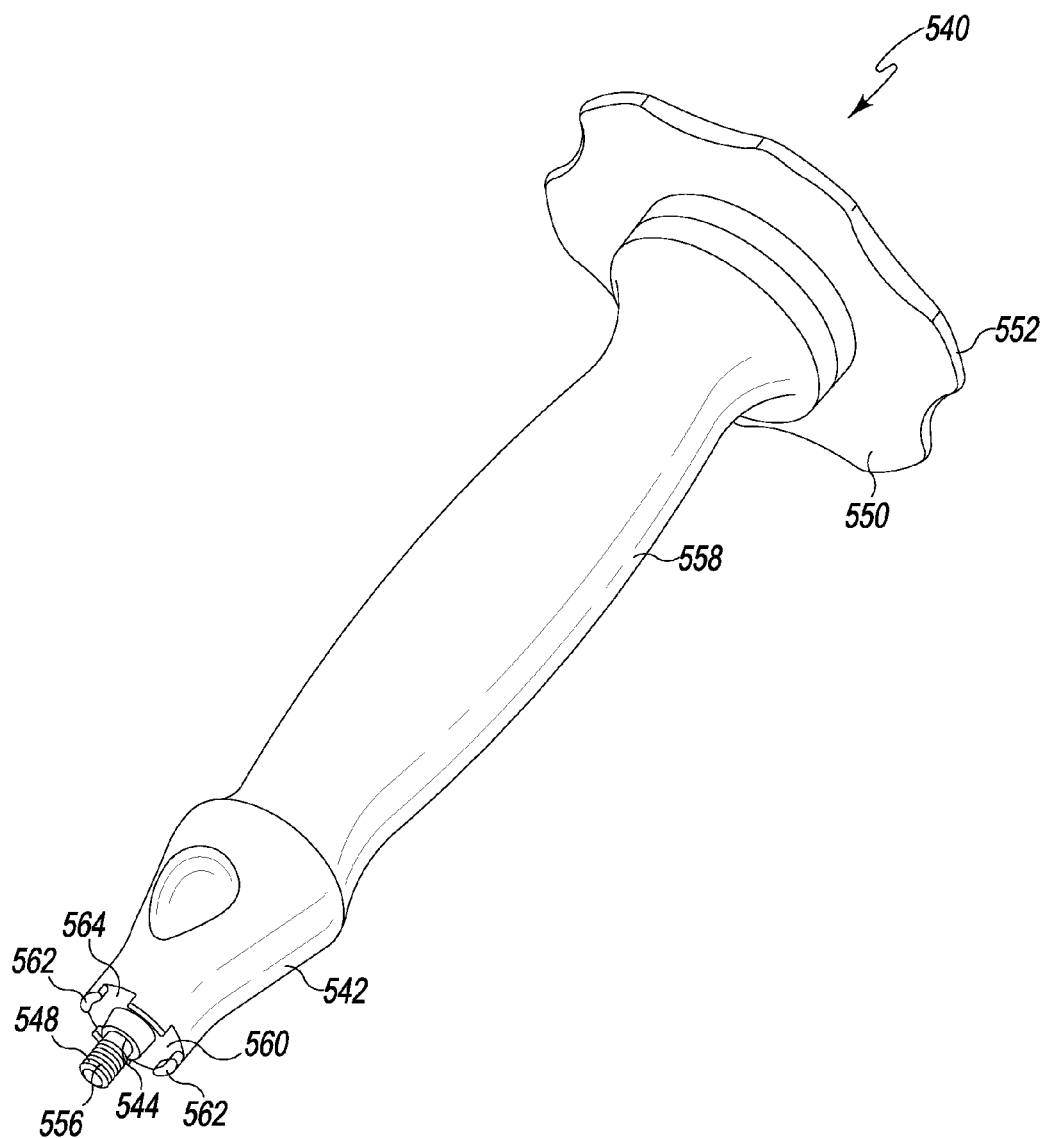
FIG. 48 is a perspective view of another implant insertion tool that may be used in a surgical procedure to implant the stemless humeral component of FIG. 1.

Referring now to FIG. 48, there is shown another embodiment of the implant insertion tool 540. The features of the embodiment illustrated in FIG. 48 are substantially similar to those discussed above in reference to the embodiment of FIG. 37. Such features are designated in FIG. 48 with the same reference numbers as those used in FIG. 37. In essence, the embodiment of FIG. 48 is substantially the same as the embodiment of FIG. 37 with a few exceptions. For example, the size of the knob 552 is larger in the embodiment of FIG. 48 to facilitate use thereof by the surgeon. Moreover, the implant insertion tool's grip is overmolded to the tool's body 542.

Referring now to FIGS. 49-52, there is shown a drill guide 710 that may be used to pre-drill the patient's surgically-prepared humeral surface prior to implantation of the stemless humeral component 10. In such a case, the surgeon may opt to subsequently punch the patient's surgically-prepared humeral surface prior to implantation of the stemless humeral component 10 in the manner described above (i.e., use the surgical punch 240 after such pre-drilling). Alternatively, the surgeon may drill the patient's surgically-prepared humeral surface in lieu of the punch procedure.

As described above, the stemless humeral component 10 may be provided in various sizes (i.e., diameters) to fit the needs of a given patient. For example, the stemless humeral component 10 may be provided in nine different sizes. Each of such differently-sized components 10 has legs of different thicknesses and lengths. As such, if discrete drill guides are used for each differently-sized stemless humeral component 10, multiple differently-sized drill guides would be required (e.g., nine differently sized drill guides would be required for nine differently-sized stemless humeral components 10). Moreover, to avoid overly thick drill guides for the smaller sizes of stemless humeral components 10, multiple different drill sizes may be required. As will be discussed below in more detail, the drill guide 710 avoids the need for such differently-sized drill guides and drills.

Figure 49:
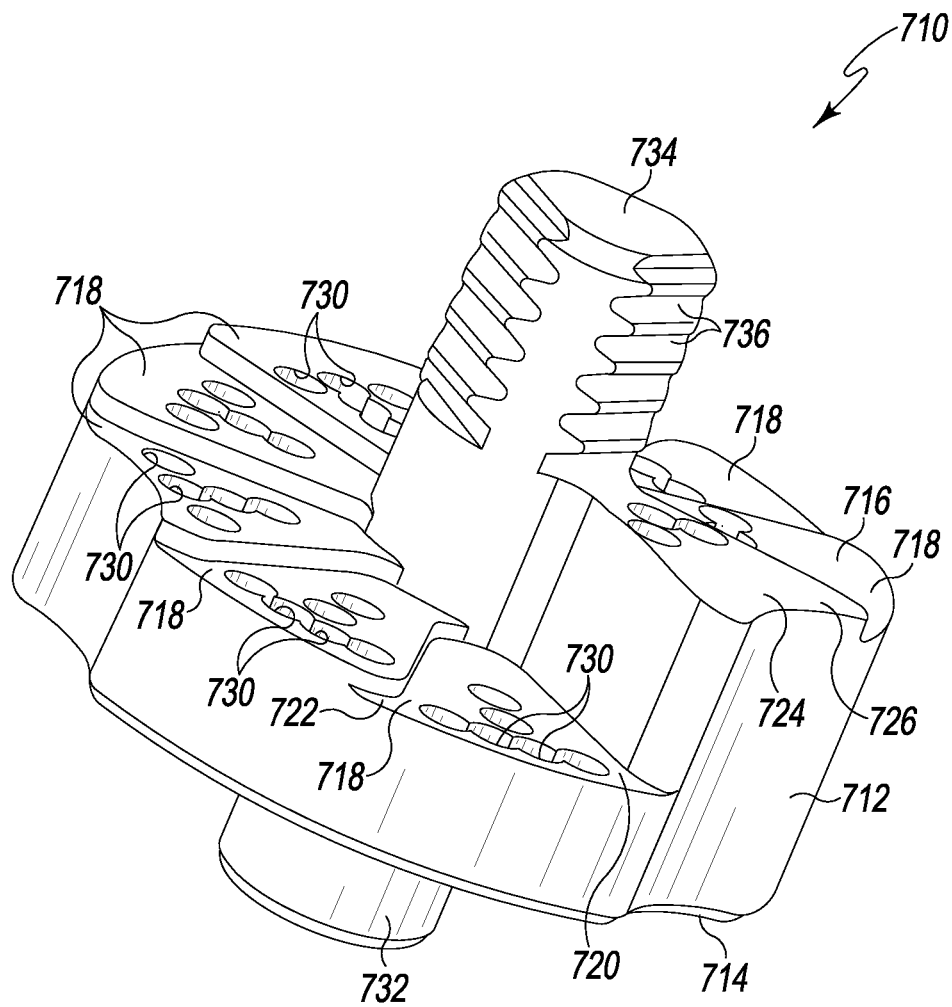
FIG. 49 is a perspective view of a drill guide that may be used in a surgical procedure to implant the stemless humeral component of FIG. 1.

The drill guide 710 includes a body 712 having a generally planar lower surface 714, and an opposite, stepped upper surface 716. As can be seen in FIG. 49, the stepped upper surface 716 is spiral shaped and, being stepped, includes a plurality of discrete generally planar drill-stop surfaces 718. Each of the drill-stop surfaces 718 is spaced apart from the lower surface 714 of the drill guide's body 712 by a different length. As a result, the drill guide's body 712 has a different thickness at the locations corresponding to each of the different drill-stop surfaces 718.

Figure 50:
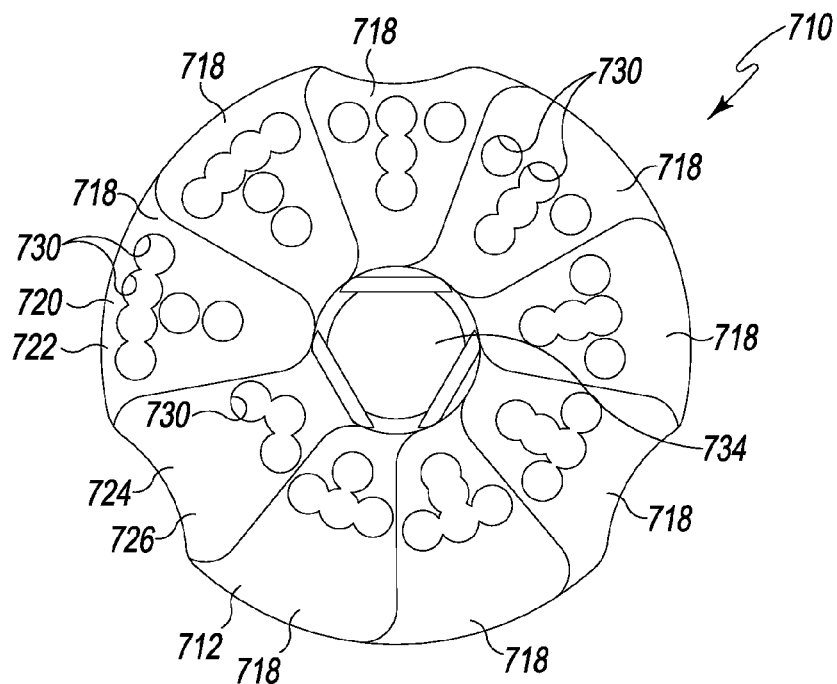
FIG. 50 is a top elevation view of the drill guide of FIG. 49.

As can be seen in FIGS. 49 and 50, each of the drill-stop surfaces 718 has a number of guide bores 730 formed therein. The guide bores 730 are configured to guide the peripheral drill bit 272 during drilling of the patient's surgically-prepared humeral surface. As such each of the guide bores 730 extends throughout the entire thickness of the guide body 712. In other words, one end of each of the guide bores 730 opens into the drill-stop surface 718, with the other end opening into the lower surface 714. As described above, the collar 284 of the peripheral drill bit 272 functions as a depth stop to ensure the drill bit 272 drills surgically-prepared holes at a desired depth. As such, the peripheral drill bit 272 may be advanced through one of the guide bores 730 and into the bone tissue until the lower surface 286 of the collar 284 bottoms out or otherwise engages the selected drill-stop surface 718.

Each of the drill-stop surfaces 718 corresponds to a differently-sized stemless humeral component 10. For example, a drill-stop surface 720 at the "bottom" end 722 of the spiral-shaped stepped upper surface 716 corresponds to the largest size of stemless humeral component 10, with the a drill-stop surface 724 at the "top" end 726 of the spiral-shaped stepped upper surface 716 corresponding to the smallest size of stemless humeral component 10. The remaining drill-stop surfaces 718 correspond to the remaining sizes of the stemless humeral component 10 with the size of the corresponding component 10 increasing along the stepped upper surface 716 in the direction from its top end 726 to its bottom end 722.

Because each of the drill-stop surfaces 718 is spaced apart from the lower surface 714 of the drill guide's body 712 by a different length, the peripheral drill bit 272 will drill to different depths of the patient's surgically-prepared humeral surface depending on which drill-stop surface 718 is used by the surgeon. For example, if the surgeon utilizes the guide holes 730 of the drill-stop surface 724 at the "top" end 726 of the spiral-shaped stepped upper surface 716, shallower drilled holes will be produced than if the surgeon utilizes the guide bores 730 of the drill-stop surface 720 at the "bottom" end 722 of the spiral-shaped stepped upper surface 716 since the collar 284 of the drill bit 272 will bottom out on the drill-stop surface 724 prior to when it will bottom out on the lower-positioned drill-stop surface 720. As such, the drill bit 272 will progressively drill deeper at the drill-stop surfaces 718 along stepped upper surface 716 in the direction from its top end 726 to its bottom end 722.

Figure 51:
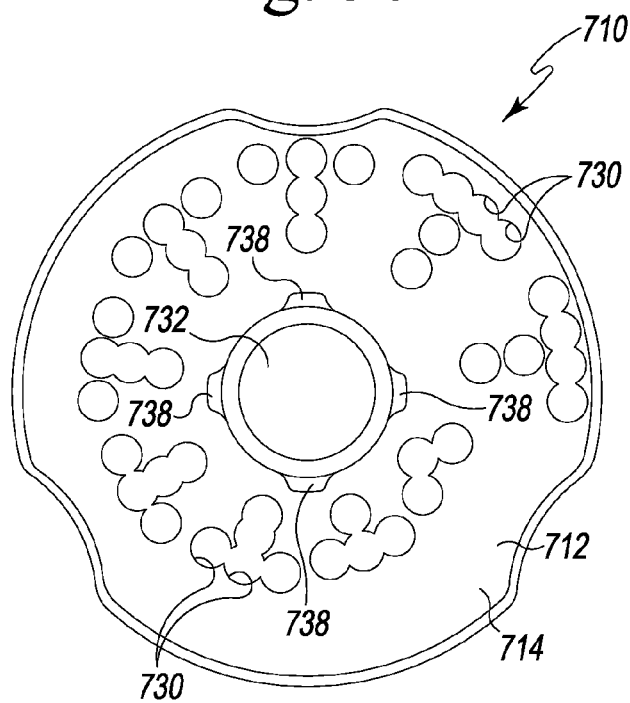
FIG. 51 is a bottom elevation view of the drill guide of FIG. 49.
Figure 52:
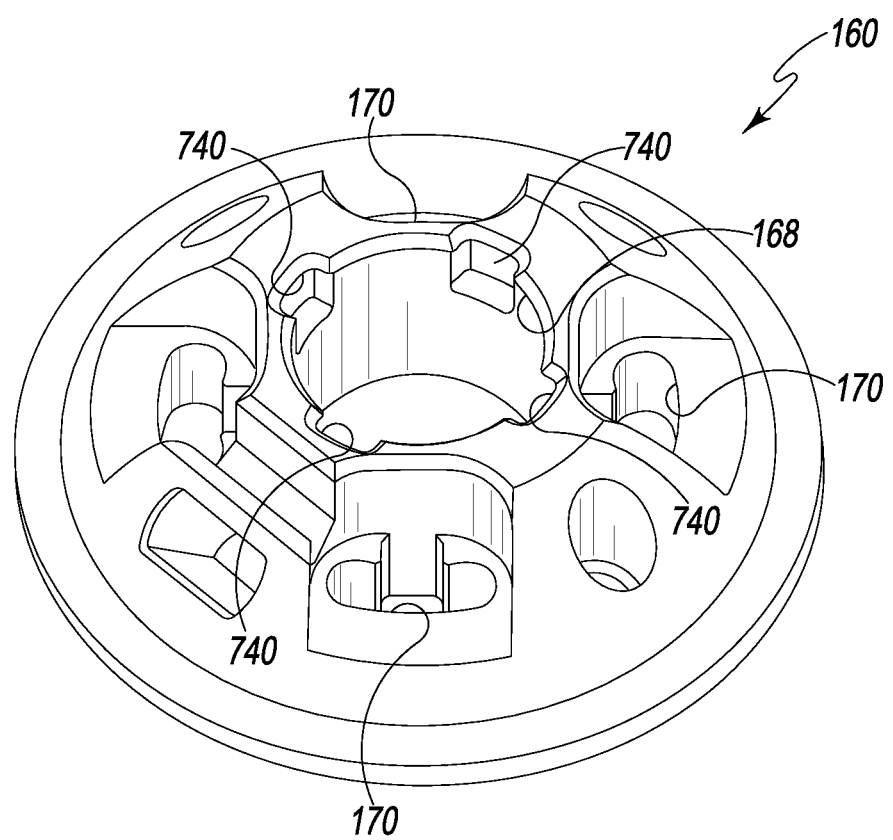
FIG. 52 is a perspective view of another embodiment of a sizing instrument that may be used in conjunction with the drill guide of FIGS. 49-51.

As can be seen in FIGS. 50 and 51, the guide bores 730 of each of the drill-stop surfaces 718 are arranged in a unique hole pattern relative to the remaining drill-stop surfaces 718. For example, the drill-stop surface 720 at the "bottom" end 722 of the spiral-shaped stepped upper surface 716 corresponding to the largest size of stemless humeral component 10 has a relatively large hole pattern (i.e., the guide bores 730 are more spread out relative to the other hole patterns), whereas the drill-stop surface 724 at the "top" end 726 of the spiral-shaped stepped upper surface 716 corresponding to the smallest size of stemless humeral component 10 has a relatively small hole pattern (i.e., the guide bores 730 are more compact relative to the other hole patterns). In such a way, the hole pattern corresponds to the size of the cantilevered legs 16 of the differently-sized stemless humeral components 10, with larger hole patterns corresponding to larger component legs 16 and smaller hole patterns corresponding to smaller component legs 16. That is, the drill-stop surfaces 718 correspond to the sizes of the stemless humeral component 10 with the size of the corresponding component 10 increasing along the stepped upper surface 716 in the direction from its top end 726 to its bottom end 722.

As can be seen in FIGS. 49 and 51, the guide body 712 has an elongated boss 732 secured to, and extending downwardly from, its lower surface 714. The elongated boss 732 is configured to be received into the elongated bore 168 of the sizing instrument 160 to secure the drill guide 710 thereto. An elongated grip 734 is secured to, and extends upwardly from, the stepped upper surface 716. The grip 734 has a number of grooves 736 formed therein and is used by the surgeon to grasp the drill guide 710.

As shown in FIG. 51, the guide body 712 has a number of alignment keys 738 formed in its lower surface 714. The alignment keys 738 are received into a number of alignment slots 740 formed in the sidewall of the sizing instrument's elongated bore 168 (see FIG. 52) to correlate the proper drill-stop surface 718 with the correct size of the sizing instrument 160. In particular, the alignment slots 740 of each of the differently-sized sizing instruments 160 are placed in annular locations unique to the particular sizing instrument 160 (i.e., each of the differently-sized sizing instruments has a unique slot configuration). When the alignment keys 738 of the drill guide 710 are advanced into the uniquely-positioned alignment slots 740, the proper drill-stop surface 718 corresponding to the particular size of the sizing instrument 160 will be positioned over one of the sizing instrument's guide punch holes 170 thereby "keying" the stepped upper surface 716 of the drill guide 710 to the particular size of the sizing instrument 160.

Like other of the instruments described herein, the drill guide 710 may be constructed with a biocompatible metal such as stainless steel, cobalt chrome, or titanium, although other metals or alloys may be used. The drill guide 710 may also be embodied as a polymer instrument. As such, drill guide 710 may be made of any suitable medical-grade polymeric material such as polyetheretherketone (PEEK). In such an embodiment, the polymer drill guide 710 may include metallic inserts (e.g., sleeves) positioned in the drill guide bores 730.

In operation, the surgeon may use the drill guide 710 to drill a number of holes in the patient's surgically-prepared humeral surface. To do so, the surgeon first selects a size of the stemless humeral component 10 to implant in the patient's humerus in the manner described above. Such a selection may be performed preoperatively or as a result of intra-operative changes based on use of the sizing instrument 160. The surgeon then secures a sizing instrument 160 that corresponds to the selected size of the stemless humeral component 10 to the surgically-prepared surface of the patient's humerus in the manner described above in regard to FIG. 27.

The surgeon then selects a drill-stop surface 718 of the drill guide 710 that corresponds to the selected size of the stemless humeral component 10 from the plurality of drill-stop surfaces 718 formed in the drill guide's stepped upper surface 716. The surgeon may then attach the drill guide 710 to the sizing instrument 160 by advancing the drill guide's elongated boss 732 into the elongated bore 168 of the sizing instrument 160. During such advancement, the alignment keys 738 of the drill guide 710 are advanced into the uniquely-positioned alignment slots 740 of the sizing instrument 160 thereby causing the drill-stop surface 718 corresponding to the particular size of the selected sizing instrument 160 to be positioned over one of the sizing instrument's guide punch holes 170.

The surgeon may then advance the peripheral drill 272 through each of the guide bores 730 of the selected drill-stop surface 718 and into the bone tissue until the drill's collar 284 bottoms out or otherwise engages the selected drill-stop surface 718. The surgeon may then rotate the drill guide 710 such that the selected drill-stop surface 718 is positioned over a different one of the remaining punch guide holes 170 of the sizing instrument 160. Thereafter, the surgeon advances the peripheral drill 272 through each of the guide bores 730 and repeats the process at each of the remaining punch guide holes 170.

The surgeon may then utilize the surgical punch 240 in a similar manner to as described above in regard to FIG. 29 to punch the now pre-drilled surgically-prepared surface of the patient's humerus and thereafter implant the stemless humeral component 10 in a similar manner to as described above in regard to FIG. 33. Alternatively, the surgeon may implant the stemless humeral component 10 into the drilled surgically-prepared surface of the patient's humerus without first utilizing the surgical punch 240.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method of performing a surgical procedure to replace the humeral head of a patient's humerus, comprising:
    resecting the humeral head of the patient's humerus so as to create a generally planar resected humeral surface comprising cancellous bone tissue surrounded by cortical bone tissue,
    forming a plurality of holes in the cancellous bone tissue of the resected humeral surface, and
    implanting a stemless humeral component into the resected humeral surface such that (i) a plurality of cantilevered legs of the stemless humeral component are positioned in the holes formed in the cancellous bone tissue of the resected humeral surface, and (ii) a circular-shaped flange of the stemless humeral component is positioned on top of the cortical bone tissue of the resected humeral surface.

2. The method of claim 1, wherein implanting the stemless humeral component comprises positioning a bottom surface of the circular-shaped flange in contact with the cortical bone tissue of the resected humeral surface.

3. The method of claim 1, wherein forming a plurality of holes in the cancellous bone tissue comprises punching the plurality of holes in the cancellous bone tissue with a surgical punch.

4. The method of claim 1, wherein forming a plurality of holes in the cancellous bone tissue comprises:
    securing a sizing instrument to the resected humeral surface, the sizing instrument having a number of punch guide holes formed therein, and
    advancing a surgical punch through the punch guide holes formed in the sizing instrument to create the plurality of holes in the cancellous bone tissue of the resected humeral surface.

5. The method of claim 1, further comprising operating a center drill to create a drilled hole in the cancellous bone tissue of the resected humeral surface, wherein:
    implanting the stemless humeral component comprises implanting the stemless humeral component into the resected humeral surface such that an elongated sleeve of the stemless humeral component is positioned in the drilled hole formed in the cancellous bone tissue of the resected humeral surface.

6. The method of claim 1, further comprising:
    inserting a tapered post of a humeral head component into a tapered bore of the implanted stemless humeral component, and
    impacting the humeral head component to taper lock the humeral head component to the implanted stemless humeral component.

7. The method of claim 1, wherein implanting the stemless humeral component comprises:
    securing the stemless humeral component to an implant insertion tool,
    positioning the implant insertion tool such that the ends of the plurality cantilevered legs of the stemless humeral component are advanced into the holes formed in the cancellous bone tissue of the resected humeral surface, and
    impacting the implant insertion tool to drive the plurality of cantilevered legs of the stemless humeral component into the holes formed in the cancellous bone tissue of the resected humeral surface.

8. The method of claim 7, wherein impacting the implant insertion tool comprises impacting the implant insertion tool to drive a bottom surface of the circular-shaped flange into contact with the cortical bone tissue of the resected humeral surface.

9. A method of performing a surgical procedure to replace the humeral head of a patient's humerus, comprising:
    resecting the humeral head of the patient's humerus so as to create a generally planar resected humeral surface comprising cancellous bone tissue surrounded by cortical bone tissue,
    securing a sizing instrument to the resected humeral surface, the sizing instrument having a number of punch guide holes formed therein,
    advancing a surgical punch through the punch guide holes formed in the sizing instrument to create a number of punched holes in the cancellous bone tissue of the resected humeral surface, and
    implanting a stemless humeral component into the resected humeral surface such that (i) a plurality of cantilevered legs of the stemless humeral component are positioned in the holes punched in the cancellous bone tissue of the resected humeral surface, and (ii) a circular-shaped flange of the stemless humeral component is positioned on top of the cortical bone tissue of the resected humeral surface.

10. The method of claim 9, wherein implanting the stemless humeral component comprises positioning a bottom surface of the circular-shaped flange in contact with the cortical bone tissue of the resected humeral surface.

11. The method of claim 9, further comprising advancing a center drill through a guide bore formed in the sizing instrument to create a drilled hole in the cancellous bone tissue of the resected humeral surface, wherein:
 implanting the stemless humeral component comprises implanting the stemless humeral component into the resected humeral surface such that an elongated sleeve of the stemless humeral component is positioned in the drilled hole formed in the cancellous bone tissue of the resected humeral surface.

12. The method of claim 9, further comprising:
 securing a trial head component to the sizing instrument prior to advancing the surgical punch, and
 trialing the shoulder joint of the patient with the trial head component.

13. The method of claim 9, wherein securing the humeral head component to the implanted stemless humeral component comprises:
 inserting a tapered post of the humeral head component into a tapered bore of the implanted stemless humeral component, and
 impacting the humeral head component to taper lock the humeral head component to the implanted stemless humeral component.

14. The method of claim 9, wherein implanting the stemless humeral component comprises:
 securing the stemless humeral component to an implant insertion tool,
 positioning the implant insertion tool such that the ends of the plurality of cantilevered legs of the stemless humeral component are advanced into the punched holes formed in the cancellous bone tissue of the resected humeral surface, and
 impacting the implant insertion tool to drive the cantilevered legs of the stemless humeral component into the punched holes formed in the cancellous bone tissue of the resected humeral surface.

15. The method of claim 14, wherein impacting the implant insertion tool comprises impacting the implant insertion tool to drive a bottom surface of the circular-shaped flange into contact with the cortical bone tissue of the resected humeral surface.

16. The method of claim 9, wherein securing the sizing instrument to the resected humeral surface comprises driving a number of spikes of the sizing instrument into the cancellous bone tissue of the resected humeral surface.

* * * * *